US012295829B2

United States Patent
Holliday et al.

(10) Patent No.: US 12,295,829 B2
(45) Date of Patent: May 13, 2025

(54) OPHTHALMIC IMPLANTS FOR CORRECTING VISION WITH A TUNABLE OPTIC, AND METHODS OF MANUFACTURE AND USE

(71) Applicant: STAAR Surgical Company, Lake Forest, CA (US)

(72) Inventors: Keith Holliday, Lake Forest, CA (US); Alexei V. Ossipov, San Clemente, CA (US); Julian D. Stevens, Lake Forest, CA (US)

(73) Assignee: STAAR Surgical Company, Lake Forest, CA (US)

( * ) Notice: Subject to any disclaimer, the term of this patent is extended or adjusted under 35 U.S.C. 154(b) by 294 days.

(21) Appl. No.: 17/937,076

(22) Filed: Sep. 30, 2022

(65) Prior Publication Data

US 2023/0140249 A1 May 4, 2023

Related U.S. Application Data

(60) Provisional application No. 63/262,073, filed on Oct. 4, 2021.

(51) Int. Cl.
*A61F 2/14* (2006.01)
*A61F 2/16* (2006.01)

(52) U.S. Cl.
CPC ............ *A61F 2/147* (2013.01); *A61F 2/1659* (2013.01); *A61F 2002/1696* (2015.04)

(58) Field of Classification Search
CPC ..................... A61F 2/1659; A61F 2002/1696
See application file for complete search history.

(56) References Cited

U.S. PATENT DOCUMENTS

| | | |
|---|---|---|
| 4,199,231 A | 4/1980 | Evans |
| 4,373,225 A | 2/1983 | Eckardstein et al. |
| 4,504,982 A | 3/1985 | Burk |
| 4,525,043 A | 6/1985 | Bronstein |
| 4,529,657 A | 7/1985 | Franz |
| 4,596,578 A | 6/1986 | Kelman |
| 4,605,409 A | 8/1986 | Kelman |

(Continued)

FOREIGN PATENT DOCUMENTS

| | | |
|---|---|---|
| BE | 1016898 A3 | 9/2007 |
| BR | 202021017763 U2 | 3/2023 |

(Continued)

OTHER PUBLICATIONS

Acrysof; Visual performance when it's needed most; 2 pages; retrieved from the internet (http://www.myalcon.com/products/surgical/acrysof-iq-iol/biomaterial.shtml) on Jun. 7, 2017.

(Continued)

*Primary Examiner* — Javier G Blanco
(74) *Attorney, Agent, or Firm* — Shay Glenn LLP

(57) ABSTRACT

Ophthalmic implants, their methods of use and manufacture. The implants may include a transparent optic portion and a peripheral non-optic portion coupled to the optic portion. The transparent optic portion may be made of a transparent optic material adapted to allow visible light to pass therethrough, and the peripheral non-optic portion may be made of a light absorbing material adapted to absorb visible light.

19 Claims, 10 Drawing Sheets

(56) References Cited

U.S. PATENT DOCUMENTS

| | | |
|---|---|---|
| 4,640,595 A | 2/1987 | Volk |
| 4,642,112 A | 2/1987 | Freeman |
| 4,681,102 A | 7/1987 | Bartell |
| 4,710,193 A | 12/1987 | Volk |
| 4,731,079 A | 3/1988 | Stoy |
| 4,752,123 A | 6/1988 | Blaker |
| 4,769,033 A | 9/1988 | Nordan |
| 4,769,035 A | 9/1988 | Kelman |
| 4,781,717 A | 11/1988 | Grendahl |
| 4,787,904 A | 11/1988 | Severin et al. |
| 4,834,750 A | 5/1989 | Gupta |
| 4,981,342 A | 1/1991 | Fiala |
| 4,990,582 A | 2/1991 | Salamone |
| 5,000,676 A | 3/1991 | Fiala |
| 5,019,098 A | 5/1991 | Mercier |
| 5,044,742 A | 9/1991 | Cohen |
| 5,073,021 A | 12/1991 | Marron |
| 5,142,411 A | 8/1992 | Fiala |
| 5,161,964 A | 11/1992 | Frigiere et al. |
| 5,192,319 A | 3/1993 | Worst |
| 5,198,844 A | 3/1993 | Roffman et al. |
| 5,217,491 A | 6/1993 | Vanderbilt |
| 5,245,366 A | 9/1993 | Svochak |
| 5,260,727 A | 11/1993 | Oksman et al. |
| 5,286,829 A | 2/1994 | Fedorov et al. |
| 5,290,892 A | 3/1994 | Namdaran et al. |
| 5,329,363 A | 7/1994 | Moskovich |
| 5,331,027 A | 7/1994 | Whitbourne |
| 5,349,396 A | 9/1994 | Roffman et al. |
| 5,359,021 A | 10/1994 | Weinschenk et al. |
| 5,410,375 A | 4/1995 | Fiala |
| 5,436,678 A | 7/1995 | Carroll |
| 5,437,647 A | 8/1995 | Firth et al. |
| 5,443,507 A | 8/1995 | Jacobi |
| 5,470,892 A | 11/1995 | Gupta et al. |
| 5,480,428 A | 1/1996 | Fedorov et al. |
| 5,485,228 A | 1/1996 | Roffman et al. |
| 5,494,484 A | 2/1996 | Feingold |
| 5,499,987 A | 3/1996 | Feingold |
| 5,517,260 A | 5/1996 | Glady et al. |
| 5,523,316 A | 6/1996 | Gan et al. |
| 5,574,518 A | 11/1996 | Mercure |
| 5,603,774 A | 2/1997 | LeBoeuf et al. |
| 5,616,148 A | 4/1997 | Eagles et al. |
| 5,620,450 A | 4/1997 | Eagles et al. |
| 5,654,349 A | 8/1997 | Feingold et al. |
| 5,654,363 A | 8/1997 | Feingold et al. |
| 5,654,388 A | 8/1997 | Feingold et al. |
| 5,661,218 A | 8/1997 | Feingold et al. |
| 5,674,282 A | 10/1997 | Cumming |
| 5,684,560 A | 11/1997 | Roffman et al. |
| 5,693,095 A | 12/1997 | Freeman et al. |
| 5,715,031 A | 2/1998 | Roffman et al. |
| 5,716,364 A | 2/1998 | Makker et al. |
| 5,766,245 A | 6/1998 | Fedorov et al. |
| 5,771,088 A | 6/1998 | Perrott |
| 5,796,462 A | 8/1998 | Roffman et al. |
| 5,800,532 A | 9/1998 | Lieberman |
| 5,807,906 A | 9/1998 | Bonvallot et al. |
| 5,814,680 A | 9/1998 | Imafuku et al. |
| 5,822,091 A | 10/1998 | Baker |
| 5,843,186 A | 12/1998 | Christ |
| 5,843,188 A | 12/1998 | McDonald |
| 5,847,802 A | 12/1998 | Menezes et al. |
| 5,856,120 A | 1/1999 | Fedorov et al. |
| 5,864,378 A | 1/1999 | Portney |
| 5,882,421 A | 3/1999 | LeBoeuf et al. |
| 5,910,537 A | 6/1999 | Feingold et al. |
| 5,913,989 A | 6/1999 | Wycliffe et al. |
| 5,922,821 A | 7/1999 | LeBoeuf et al. |
| 5,929,969 A | 7/1999 | Roffman |
| 5,947,975 A | 9/1999 | Kikuchi et al. |
| 5,982,543 A | 11/1999 | Fiala |
| 6,036,891 A | 3/2000 | Liao et al. |
| 6,045,578 A | 4/2000 | Collins et al. |
| 6,106,553 A | 8/2000 | Feingold |
| 6,110,202 A | 8/2000 | Barraquer et al. |
| 6,120,148 A | 9/2000 | Fiala et al. |
| 6,148,862 A | 11/2000 | Doll |
| 6,150,472 A | 11/2000 | Engbers |
| 6,165,490 A | 12/2000 | Fedorov et al. |
| 6,179,420 B1 | 1/2001 | Roffman et al. |
| 6,203,973 B1 | 3/2001 | Chen et al. |
| 6,238,975 B1 | 5/2001 | Fliesler et al. |
| 6,241,766 B1 | 6/2001 | Liao et al. |
| 6,244,709 B1 | 6/2001 | Vayntraub et al. |
| 6,245,106 B1 | 6/2001 | Makker et al. |
| 6,271,281 B1 | 8/2001 | Liao et al. |
| 6,386,357 B1 | 5/2002 | Egawa |
| 6,398,809 B1 | 6/2002 | Hoffmann et al. |
| 6,457,826 B1 | 10/2002 | Lett |
| 6,488,708 B2 | 12/2002 | Sarfarazi |
| 6,500,181 B1 | 12/2002 | Portney |
| 6,506,212 B2 | 1/2003 | Zhou et al. |
| 6,520,638 B1 | 2/2003 | Roffman et al. |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,557,998 B2 | 5/2003 | Portney |
| 6,576,011 B2 | 6/2003 | Portney |
| 6,576,012 B2 | 6/2003 | Lang |
| 6,609,793 B2 | 8/2003 | Norrby et al. |
| 6,709,103 B1 | 3/2004 | Roffman et al. |
| 6,737,448 B2 | 5/2004 | Liao |
| 6,790,232 B1 | 9/2004 | Lang |
| 6,802,606 B2 | 10/2004 | Roffman et al. |
| 6,899,425 B2 | 5/2005 | Roffman et al. |
| 6,923,539 B2 | 8/2005 | Simpson et al. |
| 6,957,891 B2 | 10/2005 | Fiala |
| 7,036,931 B2 | 5/2006 | Lindacher et al. |
| 7,057,816 B1 | 6/2006 | Allen et al. |
| 7,061,693 B2 | 6/2006 | Zalevsky |
| 7,073,906 B1 | 7/2006 | Portney |
| 7,118,214 B2 | 10/2006 | Cox |
| 7,157,538 B2 | 1/2007 | Callaghan et al. |
| 7,178,918 B2 | 2/2007 | Griffin |
| 7,261,412 B2 | 8/2007 | Somani et al. |
| 7,628,810 B2 | 12/2009 | Christie et al. |
| 7,789,910 B2 | 9/2010 | Knox et al. |
| 7,828,431 B2 | 11/2010 | Ho et al. |
| 7,871,162 B2 | 1/2011 | Weeber |
| 7,918,886 B2 | 4/2011 | Aharoni et al. |
| 7,997,727 B2 | 8/2011 | Ho et al. |
| 8,231,219 B2 | 7/2012 | Weeber |
| 8,425,597 B2 | 4/2013 | Glick et al. |
| 8,485,662 B2 | 7/2013 | Collins et al. |
| 8,486,055 B2 | 7/2013 | Knox et al. |
| 8,580,228 B2 | 11/2013 | Zones et al. |
| 8,617,147 B2 | 12/2013 | Knox et al. |
| 8,740,978 B2 | 6/2014 | Weeber et al. |
| 8,747,466 B2 | 6/2014 | Weeber et al. |
| 8,862,447 B2 | 10/2014 | Weeber |
| 8,894,204 B2 | 11/2014 | Weeber et al. |
| 8,911,086 B2 | 12/2014 | Dai |
| 8,974,526 B2 | 3/2015 | Bogaert |
| 9,005,281 B2 | 4/2015 | Christie et al. |
| 9,060,847 B2 | 6/2015 | Smith et al. |
| 9,144,491 B2 | 9/2015 | Knox et al. |
| 9,195,074 B2 | 11/2015 | Bakaraju et al. |
| 9,201,250 B2 | 12/2015 | Bakaraju et al. |
| 9,216,080 B2 | 12/2015 | Bogaert et al. |
| 9,220,591 B2 | 12/2015 | Zhao |
| RE45,969 E | 4/2016 | Hong et al. |
| 9,301,833 B2 | 4/2016 | Gulati et al. |
| 9,329,408 B2 | 5/2016 | Matsunaga et al. |
| 9,535,263 B2 | 1/2017 | Bakaraju et al. |
| 9,545,340 B1 | 1/2017 | Knox et al. |
| 9,557,579 B2 | 1/2017 | Lindacher et al. |
| 9,636,216 B2 | 5/2017 | Ossipov et al. |
| 9,690,882 B2 | 6/2017 | Dobschal |
| 9,717,628 B2 | 8/2017 | Vidal Canovas et al. |
| 9,733,493 B2 | 8/2017 | Wooley |
| 9,823,493 B2 | 11/2017 | Caldarise et al. |

(56) References Cited

U.S. PATENT DOCUMENTS

| | | |
|---|---|---|
| 10,004,593 B2 | 6/2018 | Webb et al. |
| 10,117,775 B2 | 11/2018 | Gulati et al. |
| 10,265,163 B2 | 4/2019 | Dudee et al. |
| 10,485,655 B2 | 11/2019 | Pinto et al. |
| 10,765,510 B2 | 9/2020 | Sarver et al. |
| 10,774,164 B2 | 9/2020 | Ossipov et al. |
| 11,427,665 B2 | 8/2022 | Ossipov et al. |
| 2001/0044657 A1 | 11/2001 | Kellan |
| 2002/0120330 A1 | 8/2002 | Galin |
| 2002/0183843 A1 | 12/2002 | Blake et al. |
| 2003/0014107 A1 | 1/2003 | Reynard |
| 2003/0063254 A1 | 4/2003 | Piers et al. |
| 2003/0081171 A1 | 5/2003 | Griffin |
| 2003/0097177 A1 | 5/2003 | Tran et al. |
| 2003/0103187 A1 | 6/2003 | Miyamura et al. |
| 2003/0187505 A1 | 10/2003 | Liao |
| 2004/0087963 A1 | 5/2004 | Ossipov et al. |
| 2005/0027354 A1 | 2/2005 | Brady et al. |
| 2005/0033422 A1* | 2/2005 | Zhao .................... A61F 2/1613 264/1.36 |
| 2005/0125000 A1 | 6/2005 | Tourrette et al. |
| 2005/0147735 A1 | 7/2005 | Lowery et al. |
| 2005/0182419 A1 | 8/2005 | Tsai |
| 2005/0203619 A1 | 9/2005 | Altmann |
| 2005/0259222 A1 | 11/2005 | Kelch et al. |
| 2006/0064162 A1 | 3/2006 | Klima |
| 2006/0089712 A1 | 4/2006 | Malecaze |
| 2006/0095127 A1 | 5/2006 | Feingold et al. |
| 2006/0098162 A1 | 5/2006 | Bandhauer et al. |
| 2006/0098163 A1 | 5/2006 | Bandhauer et al. |
| 2006/0116763 A1 | 6/2006 | Simpson |
| 2006/0167545 A1 | 7/2006 | Fiala et al. |
| 2006/0176572 A1 | 8/2006 | Fiala |
| 2006/0187413 A1 | 8/2006 | Applegate et al. |
| 2006/0200167 A1 | 9/2006 | Peterson et al. |
| 2006/0244904 A1 | 11/2006 | Hong et al. |
| 2006/0244906 A1 | 11/2006 | Piers et al. |
| 2007/0000801 A1 | 1/2007 | Mauran et al. |
| 2007/0004863 A1 | 1/2007 | Mentak |
| 2007/0168028 A1 | 7/2007 | Tran et al. |
| 2007/0258143 A1 | 11/2007 | Portney |
| 2008/0013043 A1 | 1/2008 | Ye et al. |
| 2008/0027537 A1 | 1/2008 | Gerlach et al. |
| 2008/0086208 A1 | 4/2008 | Nordan |
| 2008/0114373 A1 | 5/2008 | Rathert |
| 2008/0225409 A1 | 9/2008 | Alexay |
| 2009/0059163 A1 | 3/2009 | Pinto |
| 2009/0062911 A1 | 3/2009 | Bogaert |
| 2009/0112313 A1 | 4/2009 | Mentak |
| 2009/0157179 A1 | 6/2009 | Pinto et al. |
| 2009/0210054 A1 | 8/2009 | Weeber et al. |
| 2009/0279048 A1 | 11/2009 | Hong et al. |
| 2010/0079723 A1 | 4/2010 | Kingston et al. |
| 2010/0087921 A1 | 4/2010 | Simpson |
| 2010/0100177 A1 | 4/2010 | Zhao |
| 2010/0125279 A1 | 5/2010 | Karakelle et al. |
| 2010/0131059 A1 | 5/2010 | Callahan et al. |
| 2010/0134754 A1 | 6/2010 | Hong et al. |
| 2010/0161051 A1 | 6/2010 | Hong |
| 2010/0188636 A1 | 7/2010 | Pinto et al. |
| 2011/0046634 A1 | 2/2011 | Rathert |
| 2011/0218623 A1 | 9/2011 | Dishler et al. |
| 2011/0313519 A1 | 12/2011 | Cumming |
| 2011/0313525 A1 | 12/2011 | Cumming |
| 2012/0071888 A1 | 3/2012 | Putallaz et al. |
| 2012/0136438 A1 | 5/2012 | Moriarty |
| 2012/0158131 A1 | 6/2012 | Angelopoulos et al. |
| 2013/0090730 A1 | 4/2013 | Weeber et al. |
| 2013/0226294 A1 | 8/2013 | Van Der Mooren et al. |
| 2013/0261744 A1 | 10/2013 | Gupta et al. |
| 2014/0022508 A1 | 1/2014 | Ben-Yaish et al. |
| 2014/0135919 A1 | 5/2014 | Gontijo et al. |
| 2014/0135921 A1 | 5/2014 | Robert et al. |
| 2014/0200588 A1 | 7/2014 | Anderson et al. |
| 2014/0379078 A1* | 12/2014 | Trindade .................... A61F 2/15 623/6.17 |
| 2015/0320547 A1 | 11/2015 | Rosen et al. |
| 2015/0366656 A1 | 12/2015 | Wortz et al. |
| 2016/0067035 A1 | 3/2016 | Gontijo et al. |
| 2016/0116764 A1 | 4/2016 | Newman |
| 2016/0189570 A1 | 6/2016 | Dong et al. |
| 2016/0193040 A1 | 7/2016 | Qureshi et al. |
| 2016/0195735 A1 | 7/2016 | Bresler et al. |
| 2016/0198942 A1 | 7/2016 | Dai |
| 2016/0221283 A1 | 8/2016 | Bresler et al. |
| 2016/0228238 A1 | 8/2016 | Risser et al. |
| 2016/0302916 A1 | 10/2016 | Sarver et al. |
| 2016/0320633 A1 | 11/2016 | Weeber |
| 2016/0324629 A1 | 11/2016 | Sandstedt et al. |
| 2016/0346076 A1 | 12/2016 | Paul et al. |
| 2017/0196682 A1 | 7/2017 | Lawu |
| 2017/0245983 A1 | 8/2017 | Hong et al. |
| 2017/0245987 A1 | 8/2017 | Canovas Vidal et al. |
| 2017/0258577 A1 | 9/2017 | Pinto et al. |
| 2017/0276963 A1 | 9/2017 | Brennan et al. |
| 2017/0290657 A1 | 10/2017 | Luque |
| 2017/0319332 A1 | 11/2017 | Kahook et al. |
| 2017/0325937 A1 | 11/2017 | Weeber et al. |
| 2018/0318064 A1 | 11/2018 | Paul et al. |
| 2018/0344451 A1 | 12/2018 | Stoy |
| 2019/0076242 A1 | 3/2019 | Pinto |
| 2019/0374333 A1 | 12/2019 | Shadduck |
| 2020/0038549 A1 | 2/2020 | Stoy et al. |
| 2020/0085567 A1 | 3/2020 | Pinto et al. |
| 2020/0214830 A1 | 7/2020 | Pinto et al. |
| 2021/0093445 A1 | 4/2021 | Pinto et al. |
| 2021/0290373 A1 | 9/2021 | Peyman et al. |
| 2022/0363795 A1 | 11/2022 | Ossipov et al. |
| 2024/0008973 A1 | 1/2024 | Pinto et al. |

FOREIGN PATENT DOCUMENTS

| | | |
|---|---|---|
| CA | 2731817 A1 | 11/2009 |
| CN | 1575146 A | 2/2005 |
| CN | 1671336 A | 9/2005 |
| CN | 1835719 A | 9/2006 |
| CN | 1845712 A | 10/2006 |
| CN | 101039635 A | 9/2007 |
| CN | 101073519 A | 11/2007 |
| CN | 101199437 A | 6/2008 |
| CN | 101252895 A | 8/2008 |
| CN | 101437468 A | 5/2009 |
| CN | 101490600 A | 7/2009 |
| CN | 101796451 A | 8/2010 |
| CN | 102106764 A | 6/2011 |
| CN | 202086618 U | 12/2011 |
| DE | 102007057122 A1 | 6/2008 |
| EP | 470811 A2 | 2/1992 |
| EP | 485197 A1 | 5/1992 |
| EP | 503111 A1 | 9/1992 |
| EP | 1402852 A1 | 3/2004 |
| EP | 1424049 A1 | 6/2004 |
| EP | 1862148 A1 | 12/2007 |
| EP | 1958593 A1 | 8/2008 |
| EP | 2363426 A1 | 9/2011 |
| FR | 2745711 A1 | 9/1997 |
| JP | S58-72939 | 5/1983 |
| JP | S58-114032 A | 7/1983 |
| JP | 63-310820 | 12/1988 |
| JP | 64-002644 A | 1/1989 |
| JP | H07-184989 A | 7/1995 |
| JP | 2001235712 A | 8/2001 |
| JP | 2005002377 A | 1/2005 |
| JP | 2005523981 A | 8/2005 |
| JP | 2006510041 A | 3/2006 |
| JP | 2006515938 A | 6/2006 |
| JP | 2006522674 A | 10/2006 |
| JP | 2005062965 A | 6/2007 |
| JP | 2007536047 A | 12/2007 |
| JP | 2009525835 A | 7/2009 |
| JP | 2009528855 A | 8/2009 |
| JP | 2011041826 A | 3/2011 |
| JP | 2011519647 A | 7/2011 |

(56) References Cited

FOREIGN PATENT DOCUMENTS

| | | | |
|---|---|---|---|
| JP | 2012504785 A | 2/2012 | |
| JP | 2012517029 A | 7/2012 | |
| JP | 2013533027 A | 8/2013 | |
| JP | 2015503977 A | 2/2015 | |
| JP | 2017511169 A | 4/2017 | |
| KR | 10-20110004477 A | 1/2011 | |
| KR | 101030689 B1 | 4/2011 | |
| KR | 10-1248488 B1 | 4/2013 | |
| KR | 10-20150143634 A | 12/2015 | |
| WO | WO94/07436 A1 | 4/1994 | |
| WO | WO94/013225 A1 | 6/1994 | |
| WO | WO94/025510 A1 | 11/1994 | |
| WO | WO96/040303 A1 | 12/1996 | |
| WO | WO97/35896 A1 | 10/1997 | |
| WO | WO98/003894 A1 | 1/1998 | |
| WO | WO99/057720 A1 | 11/1999 | |
| WO | WO01/010354 A1 | 2/2001 | |
| WO | WO01/071392 A1 | 9/2001 | |
| WO | WO01/089424 A1 | 11/2001 | |
| WO | WO02/051338 A1 | 7/2002 | |
| WO | WO03/101355 A1 | 12/2003 | |
| WO | WO2004/095187 A2 | 11/2004 | |
| WO | WO2005/046527 A2 | 5/2005 | |
| WO | WO2005/099630 A1 | 10/2005 | |
| WO | WO2006/014624 A2 | 2/2006 | |
| WO | WO2006/056847 A1 | 6/2006 | |
| WO | WO2006/100086 A1 | 9/2006 | |
| WO | WO2006/108005 A2 | 10/2006 | |
| WO | WO2007/084800 A1 | 7/2007 | |
| WO | WO2007/137100 A2 | 11/2007 | |
| WO | WO2008/065573 A1 | 6/2008 | |
| WO | WO2008/077006 A1 | 6/2008 | |
| WO | WO2008/080464 A1 | 7/2008 | |
| WO | WO2009/029481 A1 | 3/2009 | |
| WO | WO2009/130610 A2 | 10/2009 | |
| WO | WO2010/100523 A1 | 9/2010 | |
| WO | WO2010/135685 A1 | 11/2010 | |
| WO | WO2011/153158 A1 | 12/2011 | |
| WO | WO2012/015300 A1 | 2/2012 | |
| WO | WO2012/083143 A1 | 6/2012 | |
| WO | WO2013/028992 A1 | 2/2013 | |
| WO | WO2013/159045 A1 | 10/2013 | |
| WO | WO2014/111769 A1 | 7/2014 | |
| WO | WO2016/025315 A1 | 2/2016 | |
| WO | WO2016/040331 A1 | 3/2016 | |
| WO | WO2016/145068 A1 | 9/2016 | |
| WO | WO2017/156077 A1 | 9/2017 | |
| WO | WO-2019217471 A1 * | 11/2019 | ........... A61F 2/1624 |
| WO | WO2020/037314 A1 | 2/2020 | |

OTHER PUBLICATIONS

Altissimo; E-beam lithography for micro-nanofabrication; Biomicrofluidics; 4 (2); 026503; doi: 10.1063/1.3437589; 6 pages; Jun. 15, 2010.

answers.com; Spherochromatism (definition); 1 page; retrieved from the internet (Answers.com) on Feb. 26, 2009.

Atchison; Design of aspheric intraocular lenses; Ophthalmic and Physiological Optics; 11(2); pp. 137-146; Apr. 1991.

Christensen; Bernard schmidt: His camera and its derivatives; 4 pages; retrieved from the internet (www.fvastro.org/articles/schmidtp2.htm) on Feb. 26, 2009.

Flat Schmidt Camera: 5 pages; retrieved from the internet (www.5f.biglobe.ne.jp/-kztanaka/flatschmidtcamera.html) on Feb. 26, 2009.

Freeman; An introduction to chromatic aberration in refractors; 4 pages; retrieved from the internet (www.maa.mhn.de/scholar/chromatic_aberration.html); on Feb. 26, 2009.

Greenbaum; Monovision pseudophakia; Journal of Cataract & Refractive Surgery; 28(8); pp. 1439-1443; Aug. 1, 2002.

Greenwall; Glass versus polycarbonate; 3 pages; retrieved from the internet (http://www.greenwallsolutions.com/installation/glass-vs-polycarbonate/) on Oct. 2012.

Liou et al.; Anatomically accurate, finite model eye for optical modeling; Journal of the Optical Society of America, Optical Society of America (US), 14(8); pp. 1684-1695; Aug. 1997.

Malyugin et al.; Gradient refractive index optics IOL: therotetical background and clinical results; Middle East African Journal of Ophthalmology; 21(1); pp. 32-39; 22 pages (Author Manuscript); Jan. 2014.

Ophthalmo Pharma; Solo Pre-Loaded IOL Injector; 11 pages; Jul. 2010.

Pfaff; Guide to making schmidt correctors; 6 pages; retrieved from the internet (www.considine.net/drowesmi/pfaff/pfaff.htm) on Feb. 26, 2009.

Smith; Improving a design; Modem Lens Design: A Resource Manual; Genesee Optics Software, Inc.; Rochester, New York: pp. 291-295;1992 (the year of publication is sufficiently earlier than the effective U.S. filing date and any foreign priority date so that the particular month of publication is not in issue).

Smith; Sec. 12.5, Archromatic Objectives (Design Forms); Modern Optical Engineering: The design of optical systems, Second Edition; McGraw-Hill; Chapter 3, pp. 375-384; 1990 (the year of publication is sufficiently earlier than the effective U.S. filing date and any foreign priority date so that the particular month of publication is not in issue).

Smith; Sec. 3.7, Aberration Correction and Residuals; Modern Optical Engineering: The design of optical systems, Second Edition; McGraw-Hill; Chapter Twelve, pp. 76-79; 1990 (the year of publication is sufficiently earlier than the effective U.S. filing date and any foreign priority date so that the particular month of publication is not in issue).

Southall; Objective of microscope; Mirrors, Prisms and Lenses: A Text-Book of Geometrical Optics; 3rd Edition; The MacMillian Company; pp. 675-677; 1933 (the year of publication is sufficiently earlier than the effective U.S. filing date and any foreign priority date so that the particular month of publication is not in issue).

Staar Surgical Company; Bank of America Merrill Lynch Health Care Conference; 19 pages; May 16, 2018.

telescope optic.net; Full-aperture schmidt corrector: Schmidt camera; 3 pages; retrieved from the internet (www.telescope-optics.net/Schmidt-camera.htm) on Feb. 26, 2009.

telescope optic.net; Secondary spectrum and spherochromatism; 3 pages; retrieved from the internet (www.telescope-optics.net/secondaryspectrum_spherochromatism.html) on Feb. 26, 2009.

Thibos: Retinal image quality and visual performance; Wavefront Congress Short Course; Indiana University, School of Optometry; 40 pages; Feb. 2008.

Wikipedia; Schmidt camera; 2 pages; retrieved from the internet (en.wikipedia.org/wiki/Schmidt_camera) on Feb. 26, 2009.

* cited by examiner

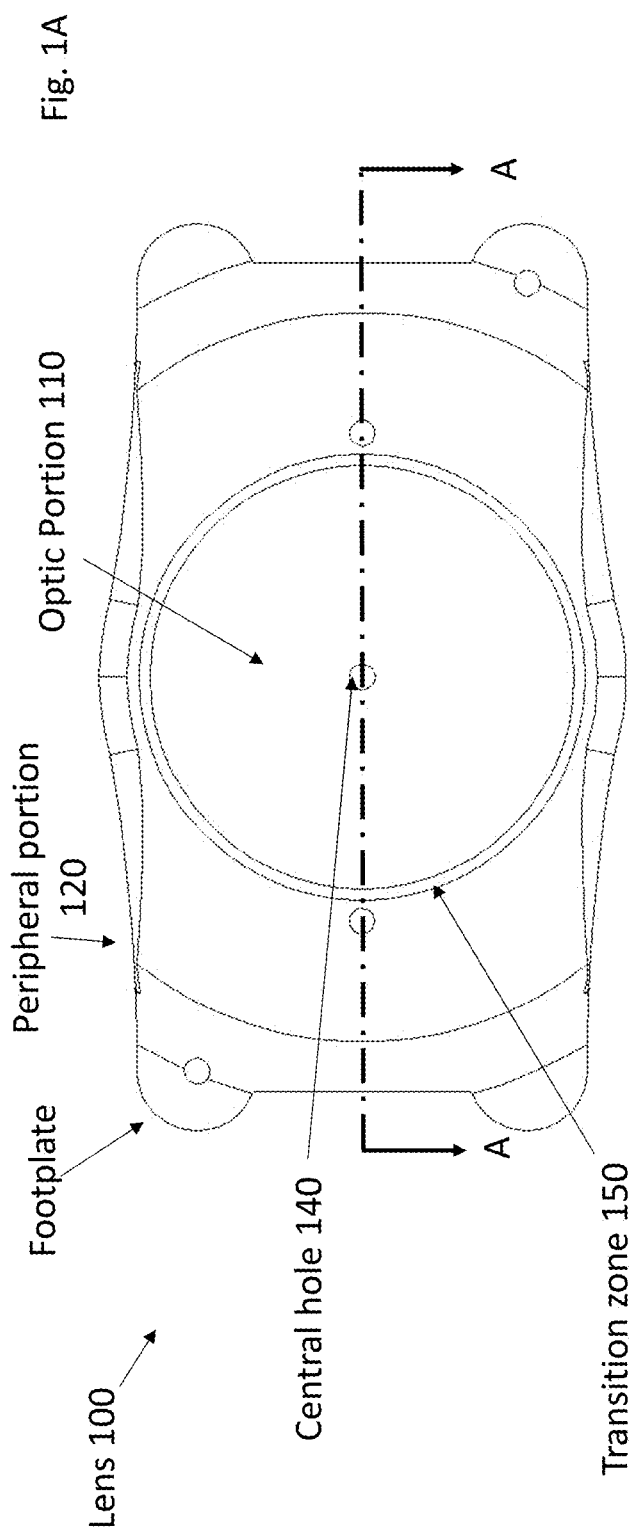
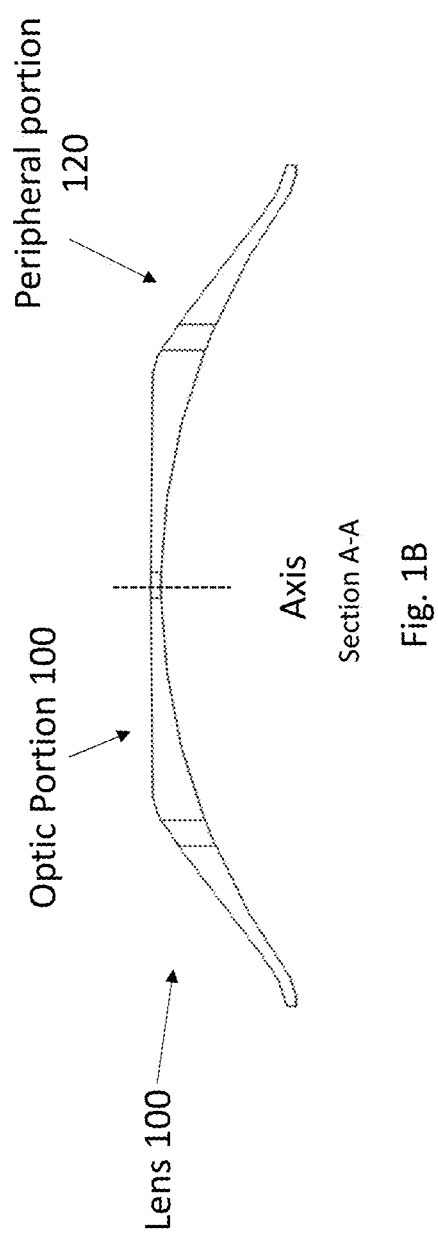

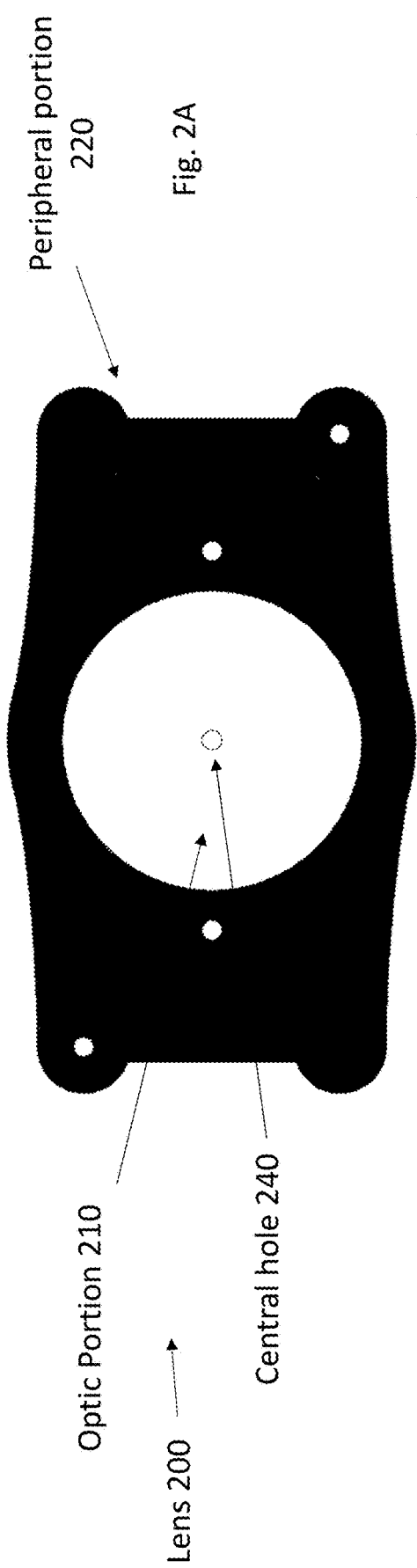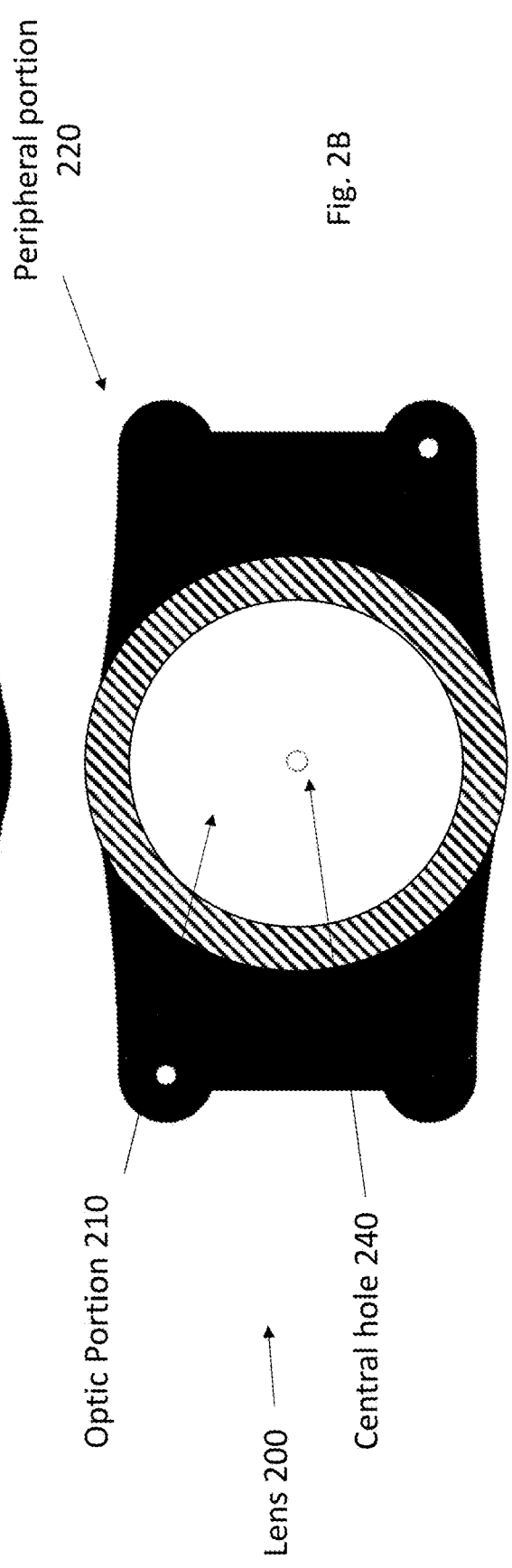

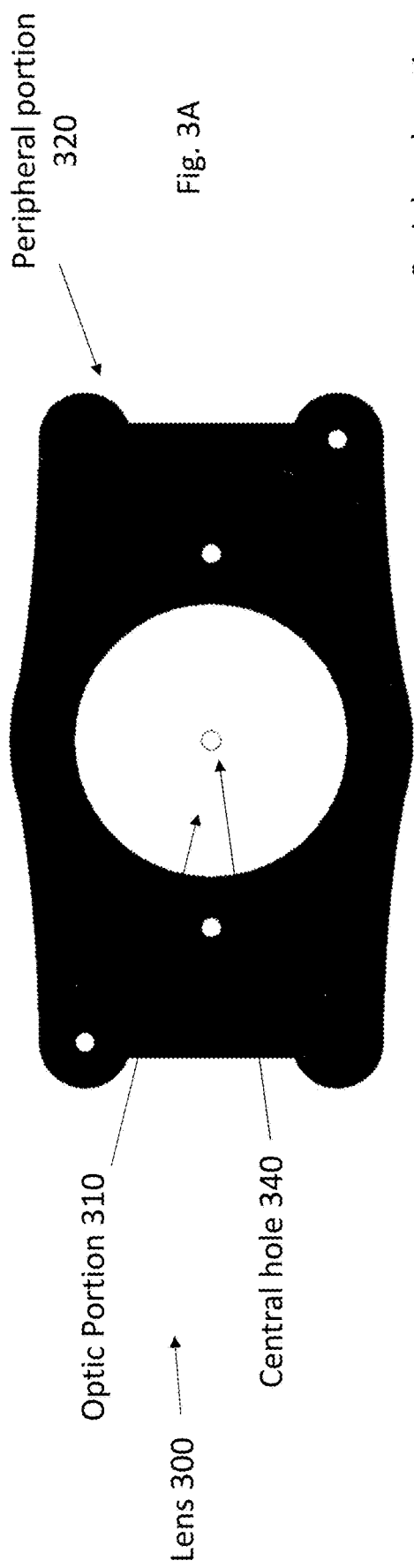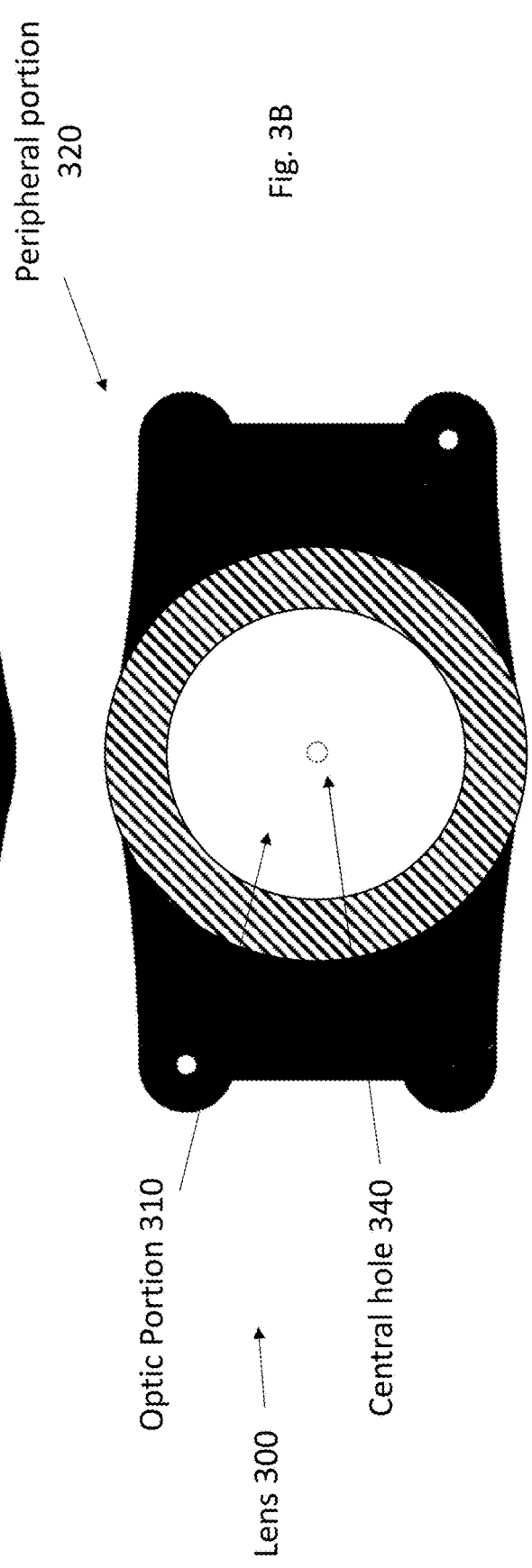

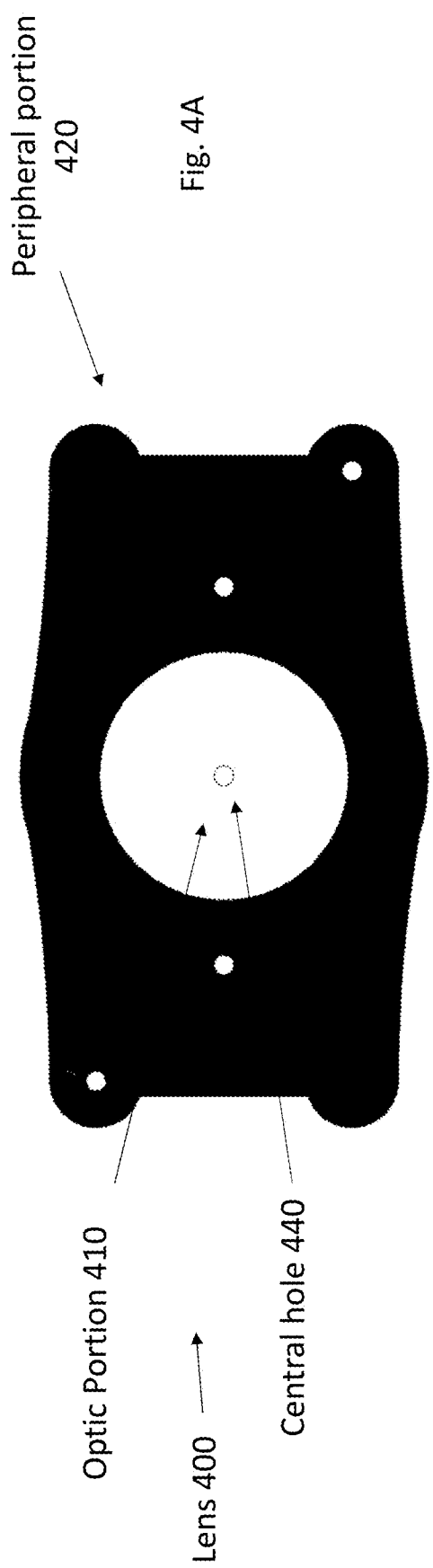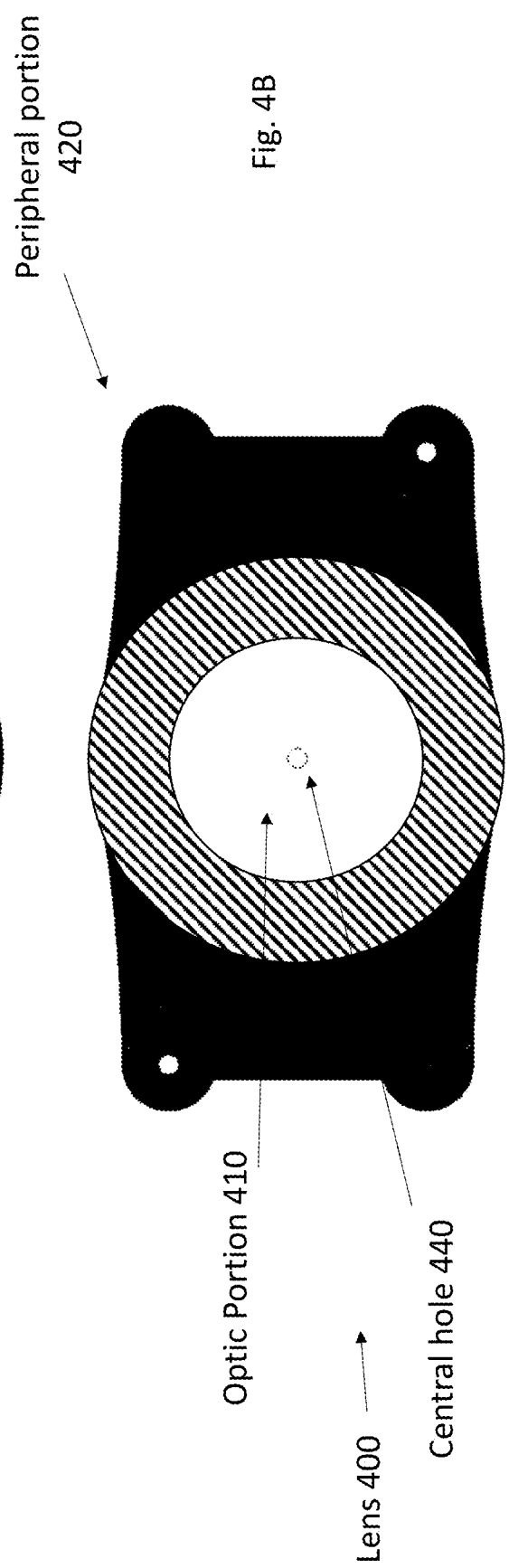

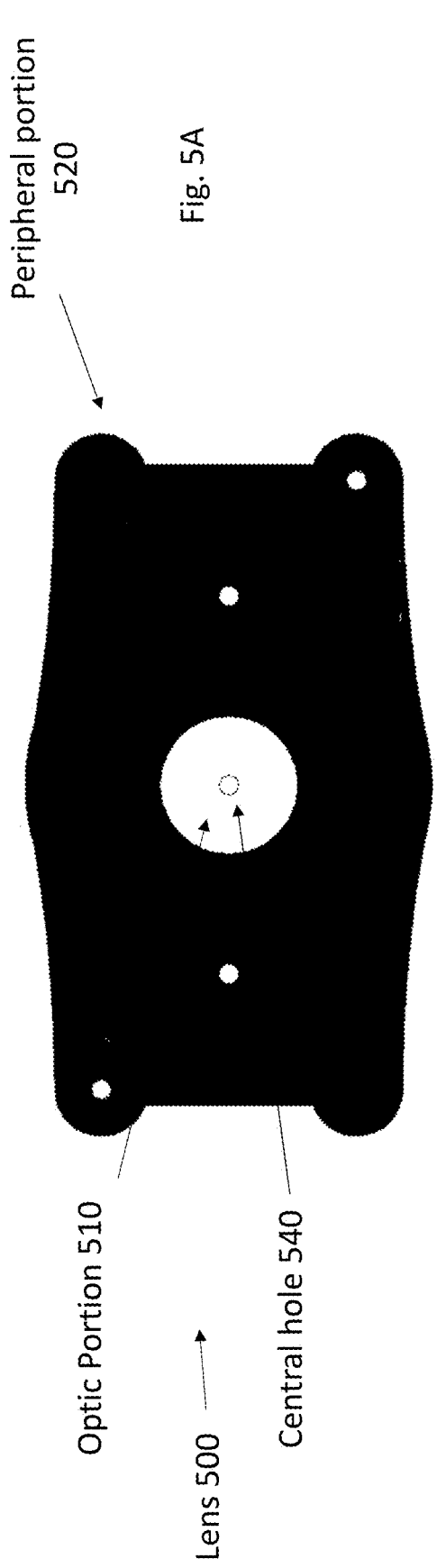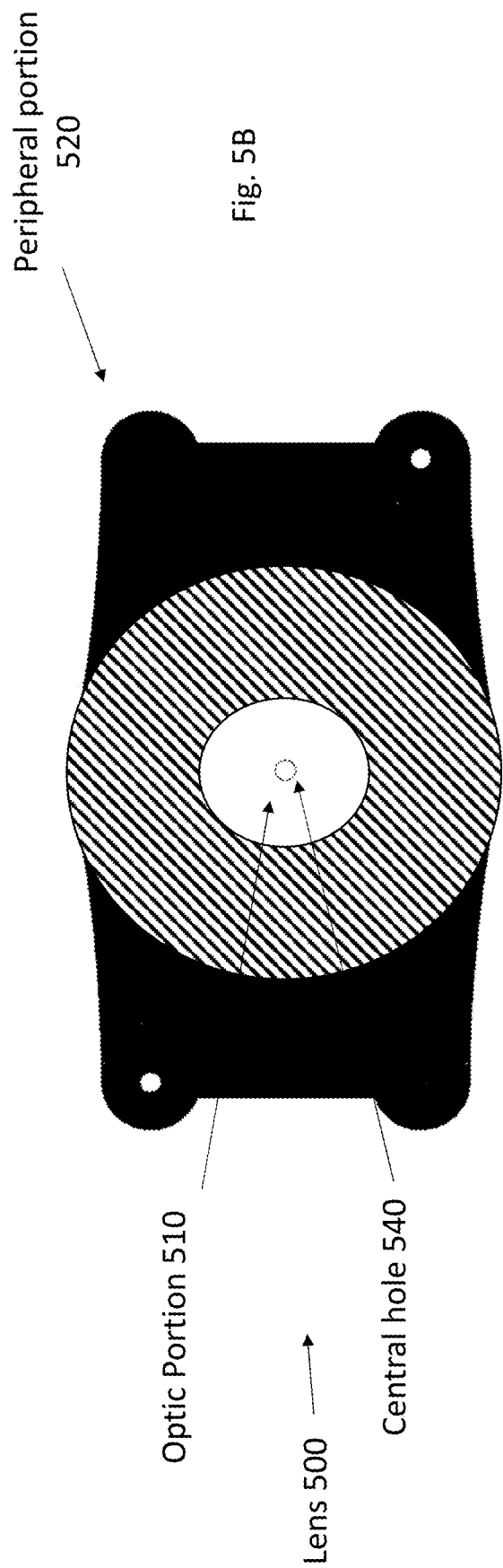

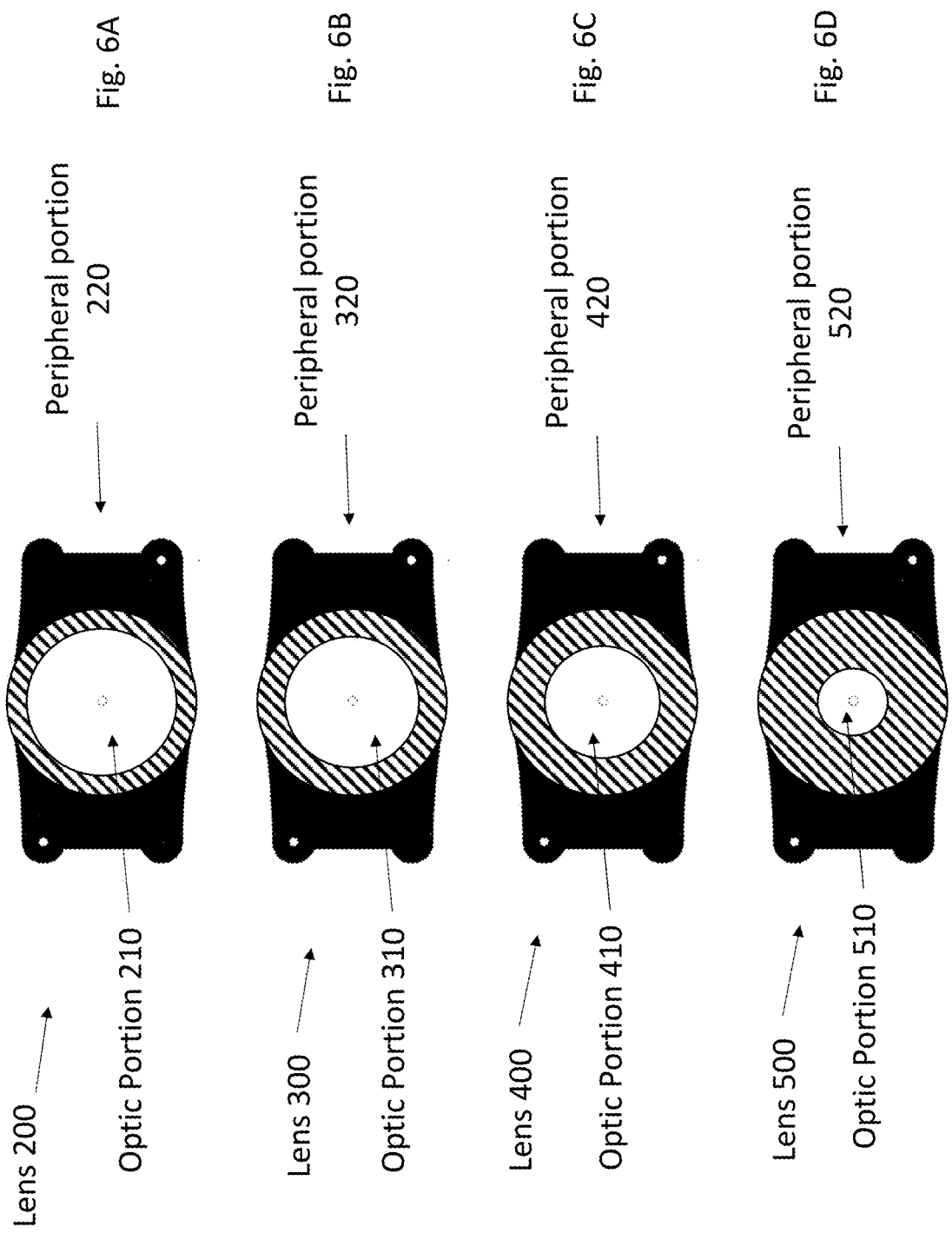

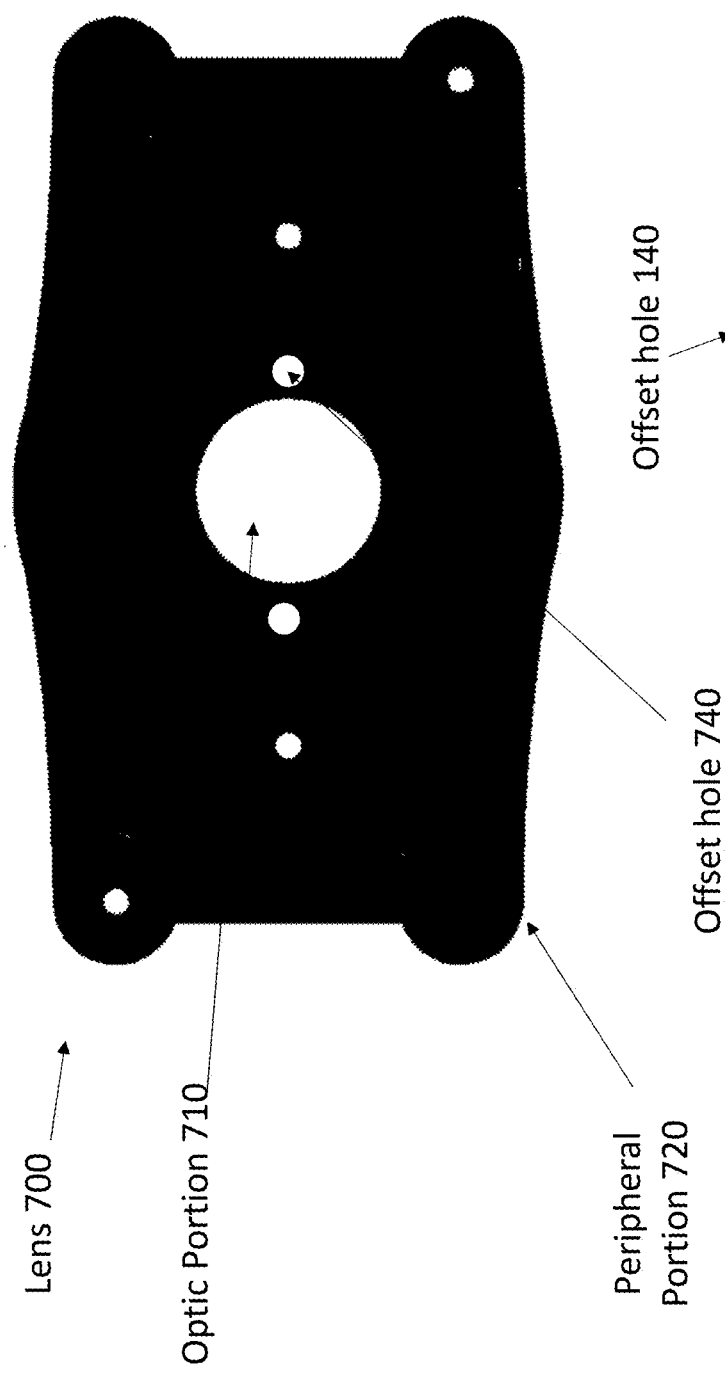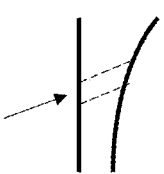

OPHTHALMIC IMPLANTS FOR CORRECTING VISION WITH A TUNABLE OPTIC, AND METHODS OF MANUFACTURE AND USE

CROSS REFERENCE TO RELATED APPLICATIONS

This application claims priority to U.S. Provisional Application 63/262,073, filed Oct. 4, 2021, the entire disclosure of which is incorporated by reference herein for all purposes.

The following references are incorporated by reference herein in their entireties for all purposes: U.S. Pat. No. 10,485,655; PCT Pub. No. WO/2017/156077; and U.S. Pub. No. 2019/0076242.

INCORPORATION BY REFERENCE

All publications and patent applications mentioned in this specification are herein incorporated by reference to the same extent as if each individual publication or patent application was specifically and individually indicated to be incorporated by reference.

BACKGROUND

There may be benefits for a peripheral portion (e.g., haptic) of an intraocular lens (e.g., an Intraocular Collamer Lens (ICL)) to be adapted to prevent or minimize visual disturbances caused by the interaction between incident light and one or more surfaces of the lens. Additionally, or alternatively, there may be benefits to providing more customization or tuning options in the design of the optic, such as, without limitation, for one or more dimensions of the optic (e.g., optic diameter, optic central thickness, or optic peripheral thickness). The disclosure herein includes lenses and methods of manufacture that are adapted to provide one or more of these benefits.

SUMMARY OF THE DISCLOSURE

One aspect of the disclosure is an ophthalmic implant, comprising: a transparent optic portion; and a peripheral non-optic portion coupled to the optic portion and extending peripherally therefrom, the peripheral portion sized and configured to engage a sulcus of an eye, the transparent optic portion made of a transparent optic material adapted to allow visible light to pass therethrough, and the peripheral non-optic portion made of a light absorbing material adapted to absorb visible light. This aspect may also include any suitably combinable feature from any implant or lens herein, including in any of the claims as filed.

One aspect of this disclosure is a monofocal ophthalmic implant, comprising: a transparent optic portion with a diameter from 4 mm to 7 mm; and a peripheral non-optic portion coupled to the optic portion and extending peripherally therefrom, the peripheral portion sized and configured to engage a sulcus of an eye, the transparent optic portion made of a transparent optic material adapted to allow visible light to pass therethrough, and the peripheral non-optic portion made of a light absorbing material adapted to absorb visible light. This aspect may also include any suitably combinable feature from any implant or lens herein, including in any of the claims as filed.

One aspect of this disclosure is an ophthalmic implant for treating presbyopia, comprising: a transparent optic portion configured as an extended depth of field optic to treat presbyopia; and a peripheral non-optic portion coupled to the optic portion and extending peripherally therefrom, the peripheral portion sized and configured to engage a sulcus of an eye, the transparent optic portion made of a transparent optic material adapted to allow visible light to pass therethrough, and the peripheral non-optic portion made of a light absorbing material adapted to absorb visible light. This aspect may also include any suitably combinable feature from any implant or lens herein, including in any of the claims as filed.

One aspect of this disclosure is a phakic intraocular lens, comprising: a transparent optic made of a transparent optic material, the optic having a power from −15 D to −30 D or from +5 D to +15 D, a diameter from 2 mm to 5 mm, and a difference between a central thickness and an edge thickness less than 500 microns; and an opaque peripheral non-optic portion made of a visible light absorbing material coupled to the optic and extending peripherally therefrom, the opaque peripheral portion sized and configured to engage a sulcus of an eye. This aspect may also include any suitably combinable feature from any implant or lens herein, including in any of the claims as filed.

One aspect of this disclosure is an intraocular lens, comprising: a transparent optic made of a transparent optic material, the optic having a diameter from 1 mm to 3 mm; and an opaque peripheral non-optic portion coupled to the optic and extending peripherally therefrom, the peripheral portion sized and configured to engage a sulcus of an eye and secure the lens in an eye. This aspect may also include any suitably combinable feature from any implant or lens herein, including in any of the claims as filed.

One aspect of this disclosure is a method of correcting vision, comprising: positioning a lens into a posterior chamber of an eye, the lens including, a transparent optic made of a transparent optic material, and an opaque peripheral non-optic portion coupled to the optic and extending peripherally therefrom, the peripheral non-optic portion made of a light absorbing material adapted to absorb visible light, and sized and configured to engage a sulcus of an eye and secure the lens in an eye, wherein positioning the lens into the posterior chamber comprises interfacing the peripheral portion with the sulcus of the eye to secure the lens in the eye, and causing the opaque peripheral non-optic portion to absorb visible light that is incident upon the opaque peripheral non-optic portion. This aspect may also include any suitably combinable feature from any method herein, including in any of the claims as filed.

One aspect of this disclosure is a method of implanting a monofocal lens, comprising: positioning a monofocal lens into a posterior chamber of an eye, the lens including a transparent optic portion made of a transparent optic material adapted to allow visible light to pass therethrough, the optic portion having a diameter from 4 mm to 7 mm, and an opaque peripheral non-optic portion made of a light absorbing material adapted to absorb visible light, the peripheral non-optic portion coupled to the optic portion and extending peripherally therefrom, wherein positioning the monofocal lens into the posterior chamber comprises interfacing the peripheral portion with the sulcus of the eye to secure the lens in the eye, and causing the peripheral portion to absorb visible light that is incident upon the peripheral portion. This aspect may also include any suitably combinable feature from any method herein, including in any of the claims as filed.

One aspect of this disclosure is a method of treating presbyopia, comprising: positioning a lens into a posterior chamber of an eye, the lens including a transparent optic portion configured as an extended depth of field optic to treat presbyopia, the optic portion made of a transparent optic material and having a diameter from 3 mm to 5 mm, and an opaque peripheral non-optic portion made of a light absorbing material adapted to absorb visible light, and the peripheral portion coupled to the optic portion and extending peripherally therefrom, wherein positioning the lens into the posterior chamber comprises interfacing the peripheral portion with the sulcus of the eye to secure the lens in the eye, and causing the peripheral portion to absorb visible light that is incident upon the peripheral portion. This aspect may also include any suitably combinable feature from any method herein, including in any of the claims as filed.

One aspect of this disclosure is a method of implanting a phakic lens, comprising: positioning a phakic lens into a posterior chamber of an eye, the phakic lens including a transparent optic portion made of a transparent optic material, the optic portion having a power from −15 D to −30 D or from +5 D to +15 D, a diameter from 2 mm to 5 mm, and a difference between a central thickness and an edge thickness less than 500 microns, and an opaque peripheral non-optic portion made of a visible light absorbing material and coupled to the optic portion and extending peripherally therefrom, wherein positioning the phakic lens into the posterior chamber comprises interfacing the peripheral portion with the sulcus of the eye to secure the lens in the eye, and causing the peripheral portion to absorb visible light that is incident upon the peripheral portion. This aspect may also include any suitably combinable feature from any method herein, including in any of the claims as filed.

One aspect of this disclosure is a method of providing vision correction to a patient, comprising: in a patient in which an eye is aberrated, positioning a lens into a posterior chamber of an eye, the lens including a transparent optic portion made of a transparent optic material, the optic portion having a diameter from 1 mm to 3 mm, and an opaque peripheral non-optic portion made of a visible light absorbing material and coupled to the optic portion and extending peripherally therefrom, wherein positioning the phakic lens into the posterior chamber comprises interfacing the peripheral portion with the sulcus of the eye to secure the lens in the eye, and causing the peripheral portion to absorb visible light that is incident upon the peripheral portion. This aspect may also include any suitably combinable feature from any method herein, including in any of the claims as filed.

One aspect of this disclosure is a method of manufacturing an ophthalmic lens, comprising: creating an optic rod of transparent optic material; creating a peripheral portion rod made of visible light absorbing material adapted to absorb light; forming a cylindrical channel in the peripheral portion rod; positioning the optic rod into the cylindrical channel; and adhering the optic rod to the peripheral portion rod to form an adhered rod with a central transparent region and a peripheral visible light absorbing region. This aspect may also include any suitably combinable feature from any method herein, including in any of the claims as filed.

One aspect of this disclosure is a method of manufacturing an ophthalmic lens, the method comprising: positioning an optic rod into a cylindrical channel that extends through a peripheral non-optic portion rod, the optic rod made of transparent optic material and the peripheral portion rod made of a visible light absorbing material; and adhering the optic rod to the peripheral portion rod to form a composite rod with a central transparent region and a peripheral visible light absorbing region. This aspect may also include any suitably combinable feature from any method herein, including in any of the claims as filed.

One aspect of this disclosure is an intraocular lens, comprising: a transparent optic portion and a non-optic peripheral portion comprising a visible light absorbing material, wherein the optic portion has an axis that is offset from and parallel to a peripheral portion axis. This aspect may also include any suitably combinable feature from any lens herein, including in any of the claims as filed.

One aspect of this disclosure is an intraocular lens, comprising: a transparent optic portion and a non-optic peripheral portion comprising a visible light absorbing material, the non-optic peripheral portion comprising one or more apertures therethrough adjacent the optic, the one or more apertures angled towards the periphery of the lens. This aspect may also include any suitably combinable feature from any lens herein, including in any of the claims as filed.

One aspect of this disclosure is an intraocular lens, comprising: a transparent optic portion and a non-optic peripheral portion comprising a visible light absorbing material, the non-optic peripheral portion comprising one or more apertures therethrough and adjacent the optic, the one or more apertures each having an axis that is not parallel with an optic portion axis. This aspect may also include any suitably combinable feature from any lens herein, including in any of the claims as filed.

BRIEF DESCRIPTION OF THE DRAWINGS

FIGS. 1A and 1B are top (anterior) and side views, respectively, of an exemplary lens with a transparent optic made of a transparent material adapted to allow visible light to pass therethrough, and the peripheral non-optic portion also made of a transparent material adapted to allow visible light to pass therethrough.

FIGS. 2A and 2B illustrate a top (anterior) view of an exemplary lens with a transparent optic made of a transparent material adapted to allow visible light to pass therethrough, and a peripheral non-optic portion made of a light absorbing material adapted to absorb visible light.

FIGS. 3A and 3B illustrate an exemplary lens with a transparent optic made of a transparent material adapted to allow visible light to pass therethrough, and a peripheral non-optic portion made of a light absorbing material adapted to absorb visible light.

FIGS. 4A and 4B illustrate an exemplary lens with a transparent optic made of a transparent material adapted to allow visible light to pass therethrough, and a peripheral non-optic portion made of a light absorbing material adapted to absorb visible light.

FIGS. 5A and 5B illustrate an exemplary lens with a transparent optic made of a transparent material adapted to allow visible light to pass therethrough, and a peripheral non-optic portion made of a light absorbing material adapted to absorb visible light.

FIGS. 6A, 6B, 6C and 6D illustrate exemplary lenses each with a transparent optic made of a transparent material adapted to allow visible light to pass therethrough, and a peripheral non-optic portion made of a light absorbing material adapted to absorb visible light.

FIG. 7A illustrates an exemplary lens with a relatively small diameter optic, and peripheral portion apertures.

FIG. 7B illustrates a side view of a portion of an exemplary lens from FIG. 7A, including one of the peripheral apertures.

DETAILED DESCRIPTION

Figure 9:
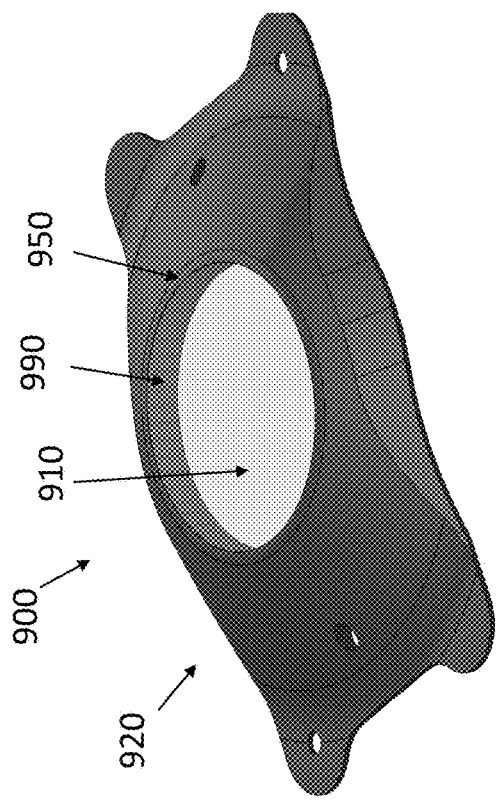
FIGS. 8 and 9 illustrate renderings of exemplary manufactured lenses with transparent optics made of a transparent material adapted to allow visible light to pass therethrough, and peripheral non-optic portions made of a light absorbing material adapted to absorb visible light.

The disclosure is related to ophthalmic implants, such as lenses that are configured for placement into an eye. By way of example only, some lenses herein may be configured to be placed in a posterior chamber of an eye, between an iris and a capsular bag. Lenses herein may optionally be configured as extended depth of field lenses. Concepts herein may also be applicable to lenses implanted in other parts of an eye, and may be applicable to lenses configured for a variety of types of vision correction (e.g., presbyopia, myopia, astigmatism, corneal damage or disease, lenticular damage or disease etc.).

One aspect of this disclosure is related to implantable lenses configured for correcting vision, wherein the optic is tunable, or adaptable as needed for a particular therapeutic application. Lenses herein may include a peripheral, non-optic portion coupled to a transparent optic. The peripheral portions herein may generally be referred to herein as haptic portions, and they may comprise one or more haptics. The peripheral portions generally provide structural support to the ophthalmic implant, and are generally sized and disposed relative to the optic to engage tissue (e.g., the sulcus) and centrally locate the optic.

The lenses described herein also include a transparent optic that comprises a transparent optic material adapted to allow light to pass therethrough and to the retina. The transparent material may comprise, for example, silicone, acrylics, or hydrogels. The transparent material may comprise hydrophobic or hydrophilic material. The transparent material may comprise Collamer®.

The lenses herein may include a peripheral non-optic portion that is made of a visible light absorbing material adapted to absorb visible light. The visible light absorbing material of the peripheral portions may include one or more constituent components or agents that impart visible light absorbing properties to the light absorbing material, such as one or more of titanium, obsidian, gold, titanium dioxide, silicon carbide, carbon, charcoal or soot or organic chromophores that absorb light across the visible part of the electromagnetic spectrum.

In some mere examples, the peripheral non-optic portions may include one or more of the same components or agents as the optic portion, while also including the one or more visible light absorbing components or agents. For example only, peripheral portions herein may comprise silicone, acrylics, or hydrogels, as well as one or more of titanium, obsidian, gold, titanium dioxide, silicon carbide, carbon, charcoal or soot or organic chromophores. In some examples only, the optic and peripheral material may comprise the same or substantially the same components, except that the peripheral portion material may include the one or more visible light absorbing components or agents. For example only, an optic may comprise Collamer®, while the peripheral portion may comprise Collamer® as well as one or more visible light absorbing components or agents.

In some examples only, the optic material and the peripheral material may comprise the same or substantially the same components, except that the peripheral portion (which includes the one or more visible light absorbing components or agents) may not include an ultraviolet blocking chromophore that is included in the optic portion material. Since the peripheral portion includes one or more visible light absorbing components or agents, the peripheral portion may not need to include an ultraviolet radiation blocking chromophore, for example. For example only, an optic portion may comprise Collamer® while the peripheral portion may comprise Collamer® without an ultraviolet radiation blocking chromophore (as well as the one or more visible light absorbing components or agents). In some embodiments, however, it may be advantageous that the visible light blocking chromophore in the peripheral non-optic portion also blocks ultraviolet radiation. For example only, for some vision correction applications, the peripheral non-optic portion of lens may extend within the pupil (e.g., FIG. 5), and it may be advantageous that the peripheral non-optic portion also blocks ultraviolet radiation, preventing it from reaching the retina. In other embodiments, there may be little or no advantage that the visible light blocking chromophore in the peripheral non-optic portion also blocks ultraviolet radiation.

In some examples only, the organic or inorganic chromophores that provide the visible light blocking in the peripheral portion may be crosslinked with the base polymer of the peripheral portion.

The peripheral non-optic portions herein generally provide structural support to the ophthalmic implant, and are generally sized, configured and disposed relative to the optic to engage tissue (e.g., the sulcus) and centrally locate the optic (in some, embodiments below, however, the optic may not be centrally located). The peripheral portions herein may thus also be referred to as structural support portions. In some applications, it may be desired that the peripheral structural support portions of the lens have different mechanical properties than the optic portion of the lens. For example, the optic portion and the peripheral structural support portion may be made from two different materials that have different optical properties as well as different mechanical properties. For example only, it may be desired to provide peripheral portions that are stiffer than the optic portion, or it may be desired for the peripheral portions to be less stiff than the optic portion. The material for the optic and peripheral portions may thus be selected to impart the desired optical and mechanical properties for the different portions of the lens. For example only, the peripheral portion material may be substantially different than the material for the optic portion, and the peripheral portion can also include the one or more light absorbing materials.

FIGS. 1A and 1B illustrate an exemplary lens 100 that includes transparent optic portion 110, which includes central hole 140 that is sized and positioned to provide for flow of aqueous humor through the lens. Lens 100 also includes peripheral non-optic portion 120 coupled to the optic portion, extending radially therefrom, and which may optionally (but not necessarily) be made of a light absorbing material that absorbs light, as is described herein. Lens 100 also includes transition zone 150 that connects or couples the optic portion 110 to the peripheral non-optic portion 120. The transitions zones herein may be considered part of the lens that acts as a transition between the optic portion and the peripheral non-optic portion. The transition zones herein may optionally be considered part of the non-optic portion of the lens in that they are not specifically configured as part of the optic. FIGS. 1A and 2B illustrate an exemplary peripheral portion 120 that includes plate or plate-like haptics that include exemplary and optional footplates as shown, but the lenses herein may have other peripheral portion configurations.

It is noted that FIGS. 2-7 illustrate the peripheral non-optic portions as "black" regions, while FIGS. 1A and 1B are also optional examples of a lens that includes a peripheral non-optic portion with one or more visible light absorbing materials, but instead shows them without the blackened designation. It is understood that the visible light absorbing peripheral portions herein may be illustrated as blackened regions (e.g., FIGS. 2-7, which may more depict how the lens would look after manufacture) or as depicted in FIGS. 1A and 1B.

FIGS. 2A and 2B shows an exemplary lens 200 that includes a transparent optic portion 210, which includes central hole 240 that is sized and positioned to provide for flow of aqueous humor through the lens. Lens 200 also includes peripheral non-optic portion 220 coupled to the optic portion, extending radially therefrom, and which may optionally be made of a light absorbing material that absorbs light, as is described herein. Lens 200 also includes transition zone 250 that connects or couples the optic portion 210 to the peripheral non-optic portion 220. FIGS. 2A and 2B illustrate an exemplary peripheral portion 220 that includes plate or plate-like haptics that include exemplary and optional footplates as shown, but the lenses herein may have other peripheral portion configurations.

The lenses herein, including peripheral portions made of visible light absorbing material, may impart one or more advantages or benefits to the lens, as well as creating more options for tuning or adapting the optic design as desired. For example, previous peripheral portions that transmit visible light, for example transition zones, may occasionally cause visual disturbances, such as glare or halos. For example, at night, pupils will dilate to let in more light, and light interacting with the non-optical peripheral portion surfaces of the lens may cause halos or other disturbances, symptoms or dysphotopsias. Peripheral portions described herein that absorb visible light prevent light from passing therethrough and thereby prevent the visual disturbances caused by the interaction between incident light and the non-optical surfaces of the peripheral portion.

An additional exemplary benefit of incorporating light absorbing peripheral portions into the lenses herein is that it may allow for more customization or tuning in the design of the optic, such as allowing more design options for one or more dimensions of the optic portion of the lens (e.g., diameter, optic central thickness, optic peripheral thickness). In some particular applications, the lenses herein may be placed in the sulcus between the iris and the capsular bag (with the native lens or a replacement IOL in the bag). This may be a region of the eye where there is limited space, and it may be beneficial to have a relatively very thin optic portion (e.g., 200 microns or less) to occupy as little space as possible and apply as little force on the iris as possible, and to avoid contacting the crystalline lens altogether, and for the rest of the lens to also be as thin as possible to occupy as little space as possible and apply as little force on the iris, and avoid contacting the crystalline lens altogether. For example, applying forces on the iris may reduce the angle and thereby reduce the aqueous drainage through Schlemm's canal, increasing intraocular pressure. Additionally contacting the crystalline lens may induce traumatic cataract. Additionally or alternatively, for some lenses (and treatments), it may be beneficial for the optic to have a relatively small optic diameter. With respect to peripheral portions that do not include any visible light absorbing components, decreasing the diameter of the optic inherently increases the radially inward extent of the peripheral portion, which extends the non-optic surfaces of the peripheral portion further radially inward, and thereby increases the likelihood of unwanted light scattering. Incorporating one or more light absorbing components into the peripheral portion, however, as is described herein, creates a peripheral portion that prevents visible light scattering in the peripheral non-optic portion. Peripheral portions that incorporate one or more visible light absorbing components may thus extend further radially inward without causing unwanted visible light scattering. In fact, when the peripheral portion includes visible light absorbing component(s), the optic portion diameter may be decreased as much as desired without having to worry about visible light scattering off the non-optical surfaces of the peripheral portion.

As an illustration of the aforementioned design options, while optic portions in a monofocal lens (e.g., as shown in FIGS. 2A and 2B) may have relatively large diameters, it may be desirable to have optic portions for treating presbyopia (for example only) that are generally relatively smaller than those for typical monofocal lenses. For example, for some extended depth of field lenses, such as those described in U.S. Pat. Nos. 10,485,655 and 10,881,504, which are incorporated by reference herein in their entireties for all purposes, it may be beneficial to have relatively smaller optic diameters to avoid having to manage rays that are radially further from the visual axis ("Axis" shown in the side sectional view of FIG. 1B) and therefore incident on the cornea and crystalline lens at larger angles to the normal than more central rays. As a further example, for some extended depth of field lenses, such as those described in U.S. Pat. Nos. 10,485,655 and 10,881,504, which are incorporated by reference herein in their entireties for all purposes, it may be beneficial to have optic diameters that are large enough to provide different optic regions having different optical powers, wherein the regions are large enough to provide enough visible light intensity to provide bright enough images that allow the objects at different distances to be clearly seen. FIGS. 3A and 3B illustrate exemplary lens 300 that may be configured as an extended depth of field lens to treat presbyopia. Generally, having an optic diameter that can be tuned and optimized for a lens design that refracts light from different distances to focus on the retina simultaneously, even when the crystalline lens has become rigid due to presbyopia, is an advantage in providing good images from objects that lie at a range of distances from the eye, e.g. 40 cm, 67 cm, 80 cm, 2 m and in the far distance.

Monofocal ophthalmic lenses function via refracting light from anterior and posterior curved surfaces. Generally, the anterior and posterior surfaces are curved in different ways to each other that cause the lens thickness to vary across the surface of the optic, generally from thin at the center to thicker at the periphery for negatively powered lenses such as those added to the eye to correct myopia (such as those shown in FIGS. 1A and 1B), and from relatively thick at the center to relatively thin at the periphery for positively powered lenses such as those added to the eye to correct hyperopia or to replace the natural crystalline lens. It may be desirable to implant relatively high power lenses depending on the desired vision correction for the patient. Higher powered lenses (positive or negative), however, require larger variations in thickness across the surface of the optic than lower powered lenses to provide the higher power optic. An exemplary variation in optic thickness between the center and periphery is shown generally in FIG. 1B, and in one exemplary embodiment a center thickness along axis A may be 150 microns, the thickness at a radius of 1.0 mm may be 193 microns, the thickness at a radius of 1.5 mm may be 216 microns, the thickness at a radius of 2.25 mm may be 382 microns, and the thickness at a radius of 3.0 mm may be 565 microns, for example. In this example, the lens may have a power of −9.5 D. These exemplary thicknesses may also be applied to lens 200 in FIGS. 2A and 2B, for example. As the lens must have a minimum thickness at any given position across the optic to retain mechanical stability, the lenses become thicker as power increases, most strongly in the periphery for negatively powered lenses and at the center for positively powered lenses. If the lens peripheral portion does not include a visible light absorbing component, the peripheral portion cannot extend too far radially inward or unwanted scattering will generally occur as described herein. The optic portion may thus generally have a radial extent (diameter) that prevents unwanted scattering from the peripheral portion. For higher power lenses, however, the relatively larger difference in thickness between the thinner and thicker regions may cause the lens to be so thick that it undesirably interacts with the iris and/or the native lens or native lens capsule. By incorporating one or more light absorbing components into the peripheral portion, however, the problems with light scattering with the peripheral portions herein are avoided. The high power optic can thus be made to have a smaller diameter, and the periphery of the optic and the peripheral portion do not need to be as thick as if the lens did not have a light absorbing peripheral portion, which can prevent or at least minimize the likelihood of the undesired tissue interaction discussed herein. As such, it may be advantageous to have a smaller optic diameter to prevent the lens from becoming so thick that it either rubs on the crystalline lens or pushes up on the iris, or both. Being able to decrease the diameter of the optic by incorporating opaque peripheral portions as described herein can thus allow higher power lenses to be designed and safely implanted within the sulcus. The term "high power" lenses as used herein includes negative high power lenses and positive high power lenses. Negative high power lenses include lenses that are −15 D or −30 D, or from −15 D to −30 D. Positive high power lenses herein include lenses that +5 D or +15 D, or from +5 D and +15 D. It was heretofore challenging to safely implant a high power lens within a sulcus of an average sized eye. FIGS. 4A and 4B illustrate exemplary lens 400 that may be used as any of the high power lenses herein. In some embodiments, high power lenses herein (e.g., lens 400 in FIGS. 4A and 4B) may have optic diameters from 2 mm to 4 mm, such as from 2.5 mm to 3.5 mm, such as 2.5 mm, 2.6 mm, 2.7 mm, 2.8 mm, 2.9 mm, 3.0 mm, 3.1 mm, 3.2 mm, 3.3 mm, 3.4 mm, or 3.5 mm. In some embodiments, high power lenses herein may have a central thickness from 100 microns to 200 microns, such as 120 microns to 180 microns, such as 130 microns to 170 microns, such as 140 microns to 160 microns, such as 150 microns, and optionally an optic edge thickness from 200 microns to 700 microns, such 300 microns to 700 microns, such as 400 microns to 700, microns, such as 500 microns to 700 microns. In some embodiments, high power lenses (whether negative or positive) herein may have a difference between a central thickness and an edge thickness from 100 microns and 600 microns, such as from 200 microns to 600 microns, such as 300 microns to 600 microns, such as 350 microns to 550 microns.

An additional aspect of the disclosure is lenses with a transparent optic and opaque peripheral non-optic portions as described herein, wherein the optic has a relatively much smaller optic diameter, such as from 1 mm to 3 mm, such as 1 mm, 1.5 mm, 2 mm, 2.5 mm, or 3 mm, an example of which is shown in lens 500 in FIGS. 5A and 5B. The lenses in this aspect may be implanted in an eye that has poor vision due to an aberration. Such eyes may be the result of keratoconus or previous corneal transplant or physical injury or other reasons. The optic is designed to provide a refractive correction for the central portion of the eye and blocks visible light that is peripheral to the center. The visible light that reaches the retina and is focused thereupon travels only through the central portion of the eye thus blocking rays that enter through a large portion of the pupil. The restriction of the rays that reach the retina to a single portion of the eye that incorporates larger than normal perturbations to its shape allows those rays that do reach the retina to be more similar to each other and thus to create a better image than if all rays incident upon the pupil were allowed to reach the pupil. Such a lens can provide vision that is substantially improved relative to a lens that has no restrictions for eyes that require such therapeutic treatment. FIGS. 5A and 5B illustrate an exemplary ICL that has a relatively small diameter optic portion (e.g., 1 mm to 2 mm). FIG. 5A illustrates an exemplary peripheral portion 520 that is adapted to absorb visible light. FIG. 5B illustrates a region of the peripheral portion in dashed lines as a reference, wherein the dashed line region illustrates a part of the lens that could be part of the optic portion of the lens in previous lens designs. Alternatively, the lens can be designed so that the transparent optic portion of the lens is disposed in the lens such that the optic, when implanted, is situated in a non-central region of the pupil, or otherwise not centered in the pupil. This configuration may be desirable when, for example only, the central portion of the optical pathway is more aberrated than more peripheral portions, for instance when the central portion of the cornea has been selectively injured to the extent that it has been aberrated or made more opaque.

FIGS. 6A-6D illustrate the lenses from 2B, 3B, 4B, and 5B, respectively, to illustrate exemplary differences in optic portion diameter, illustrating the design options for ICL's herein when incorporating a peripheral portion that is adapted to absorb visible light. FIGS. 6A-6D illustrate how the optic and peripheral portions of lenses herein may be tuned depending on the visual impairment the lens is designed to treat. For example only, the lens in FIGS. 2B and 6A may be designed as a monofocal lens, or monofocal lens that is also shaped to correct astigmatism, and may include an optic with a diameter from 4 mm to 7 mm, such as 4.5 mm to 6.5 mm, such as 6.0 mm, for example. For example only, the lens in FIGS. 3B and 6B may be designed as an ICL adapted to treat presbyopia (such as an extended depth of field lens), or monofocal lens that is also shaped to correct ametropia, or monofocal lens that is also shaped to correct astigmatism, or monofocal lens that is also shaped to correct ametropia or astigmatism, and may include an optic portion with a diameter from 3 mm to 5 mm, such as 3.5 mm to 5 mm, such as 3.5 mm, 3.6 mm, 3.7 mm, 3.8 mm, 3.9 mm, 4.0 mm, 4.1. mm, 4.2 mm, 4.3 mm, 4.4 mm, 4.5 mm, 4.6 mm, 4.7 mm, 4.8 mm, 4.9 mm, or 5.0 mm, for example. For example only, the lens in FIGS. 4B and 6C may be designed as a high-power ICL to correct high levels of ametropia, or high levels of ametropia with astigmatism, and may have an optic portion with a diameter from 2 mm-4 mm, such as 2.5 mm-3.5 mm, such as 3.0 mm, for example. For example only, the lens in FIGS. 5B and 6D may be designed as a therapeutic ICL (examples of which are provided herein) that may also correct ametropia or ametropia with stigmatism, and may have an optic portion with a diameter from 1 mm to 3 mm, such as 1.5 mm to 2.5 mm, such as 2.00 mm, for example.

The ICL 200 in FIGS. 2A and 2B, which may be adapted as a monofocal ICL, includes a peripheral portion 220 that is opaque, which helps block visible light incident to the transition zone between the optic 110 and the peripheral portion 220.

The ICL 300 in FIGS. 3A and 3B, which may be adapted to treat presbyopia, includes a peripheral portion 320 that is opaque, the size of which helps block peripheral visible light rays to improve the image on the retina (described above), but it can also help the ICL fit into a relatively small space without damaging tissue, as well as blocking visible light incident upon a transition zone between the optic portion and the peripheral portion.

The ICL 400 in FIGS. 4A and 4B, which may be adapted as a high powered lens, includes a peripheral portion 420 that is opaque, the size of which the lens fit into a relatively small space without damaging tissue (described above), as well as blocking light incident upon a transition zone between the optic portion 410 and the peripheral portion 420.

The ICL 500 in FIGS. 5A and 5B, which may be adapted as a therapeutic lens, includes a peripheral portion 520 that is opaque, the size of which helps block mid-peripheral and peripheral rays to improve the image on the retina (described above), and which may also help the lens fit into a relatively small space without damaging tissue (described above), as well as blocking visible light incident upon a transition zone between the optic portion 510 and the peripheral portion 520.

In some embodiments, the lenses herein with peripheral opaque regions may also be adapted to provide correction of astigmatism through the use of a lens that includes cylindrical power. Such lenses are not radially symmetrical but have an axis about which the lens thickness varies. Such lenses can benefit from the innovative concepts described herein in the same way that the spherical lenses benefit.

The exemplary benefits set forth directly above illustrate the design and tuning options provided by incorporating an opaque peripheral portion to the ICLs herein.

As described in more detail below, lenses herein may include a transparent optic and a peripheral non-optic portion made of a visible light absorbing material that is different than the optic portion material. Lenses, when made from hydrophylic materials, when implanted into the aqueous environment of the eye, or when stored in a fluid for transportation, for instance balanced salt solution, will swell to some extent relative to the lens in its unhydrated state. If one of the optic and peripheral non-optic portions swells more than the other, the coupling region between the optic and non-optic portions may be stressed or otherwise compromised after implantation. This may cause the lens, including the optic and/or the peripheral portion, to assume an undesired configuration after implantation, such as due to buckling between the optic and the non-optic portions, which may cause the lens to perform sub-optimally. Additionally, different relative swelling may apply forces to the bond between the optic and periphery, which may cause the optic and peripheral portion to detach from each other. The optic and peripheral portions herein may thus have swell indices that are the same or substantially the same so that when they are manufactured, packaged and/or implanted, they will swell to as close to the same extent as possible. The phrase swell index as used herein may also be referred to as an expansion factor, or other similar phrase. Swell index as used herein generally refers to the extent to which a material swells after being exposed to the natural aqueous humor of the eye, or similar solution such as Balanced Salt Solution (BSS), and may optionally be characterized generally by a change in linear dimensions, or volume, or change in weight, before and after swelling.

In any of the examples herein, the transparent optic material and the visible light absorbing material may have swell indices that are the same as each other. In any of the examples herein, the transparent optic material and the visible light absorbing material may have linear swell indices that are within about 5% of each other, such as within 5% of each other, or preferably within 1% of each other. As set forth above, the material of the optic portion may be substantially the same as the material of the peripheral portion. As an example, an optic may comprise Collamer®, and the peripheral portion may comprise Collamer® and may or may not include an ultraviolet radiation blocking chromophore. In these examples, the materials may not be exactly the same, but they may have swell indices within about 5% of each other. When the disclosure herein refers to materials that have swell indices that are within a certain percentage of each other, such as within 5% of each other, or preferably within 1% of each other, it is referring to the linear swell index, or how much bigger the material becomes in the linear direction. To measure a swell index in a particular fluid, for example, a material can be prepared (dry), then exposed to the fluid, and then measured to determine how much larger it has become in the linear direction.

For example only, a first optic material may have a swell index of 1.21 in BSS. Swell indices within 5% of 1.21 would include from 1.15-1.27 in BSS. Swell indices within 1% of 1.21 would include from 1.20-1.22. These are merely examples of swell indices that are within 5% and 1% of each other, respectively.

The central hole 140 (and other lens holes herein, central or otherwise) allows aqueous humor to flow throughout the eye in a manner similar to the flow of aqueous humor in an eye that does not contain a lens as described herein. The central hole is positioned centrally in order to minimize optical disturbances that occur due to visible light scatter from the walls or entry or exit of the hole but its position does not eliminate scatter entirely. In order to allow the flow of aqueous humor, the hole must be positioned within the pupil of the eye during most of the time as the iris changes size. For lenses that have relatively smaller optic regions (for example only, lens 500 in FIGS. 5A and 5B), the one or more holes 740 may advantageously be positioned in the visible light-absorbing region 720 of the lens close to but radially outside of the optic region 710 (as shown in exemplary lens 700 in FIGS. 7A and 7B) such that aqueous humor can flow through the one or more holes 740 for sufficient time to prevent pressure build-up in the eye, but by angling the one or more hole 740 towards the lens peripheral and away from the retina (as shown in the sectional partial view in FIG. 7B), scattered light will not be bothersome to the lens recipient. The central axis of the hole may be tilted or angled relative to the optical axis of the lens in a direction that is away from the fovea at an angle (e.g., FIGS. 7A and 7B) that is, in some embodiments, between 10 degrees and 45 degrees (e.g., FIG. 7B). In some embodiments the one or more angled holes may have a diameter from 100 microns to 500 microns, such as from 200 microns to 400 microns, such as from 250 microns to 400 microns (e.g., 300 microns).

Figure 8:
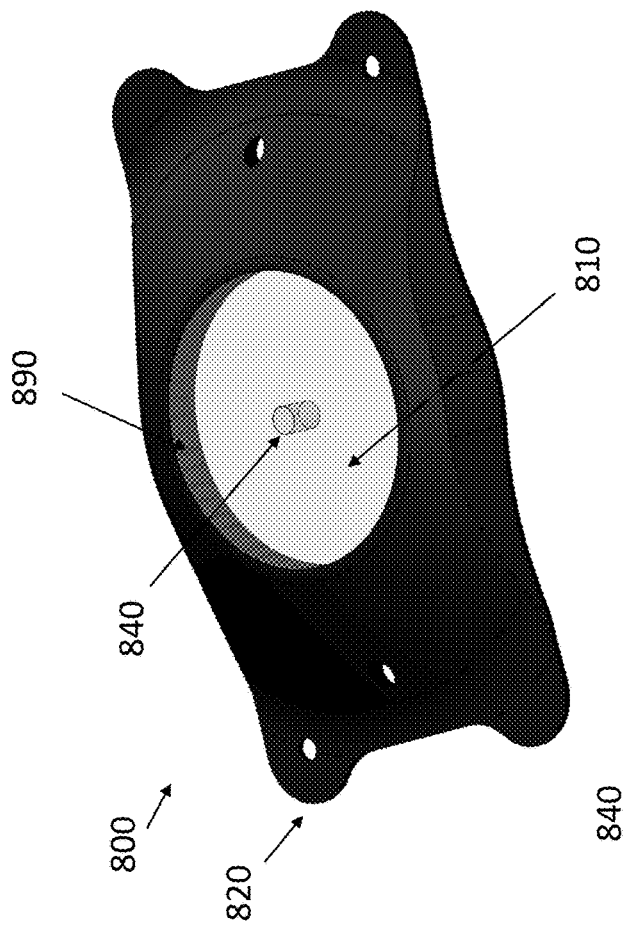

FIG. 8 illustrates a rendering of a manufactured exemplary lens 800, which includes optic portion 810 and peripheral portion 820. FIG. 8 is an anterior view of the lens. Peripheral portion 820 is made of a visible light absorbing material, as is described herein, and optic portion 810 is made of a transparent material. Any of the disclosure herein related to any aspect of any of the lenses herein may be incorporated by reference into exemplary lens 800. Lens 800 also includes a central aperture 840, and transition zone 850, which is considered part of the non-optic peripheral portion 820. FIG. 8 illustrates coupling or bonding location 890, generally referring to the annular region where a periphery of the optic portion 810 is coupled to or bonded to an inner region of the peripheral portion 820 (exemplary methods of manufacture are described herein). Lens 800 may optionally include any other suitably combinable feature of any of the lenses herein, including any of the dimensions and may also be adapted for any of the vision corrections herein. In this example, the optic axis passes through the central aperture 840.

FIG. 9 illustrates a rendering of a manufactured exemplary lens 900, which may be the same or similar to lens 800 in any regard. Lens 900 includes a transparent optic 910 coupled to opaque peripheral portion 920. Peripheral portion 920 is made of a visible light absorbing material, as is described herein, and optic portion 910 is made of a transparent material. Any of the disclosure herein related to any aspect of any of the lenses herein may be incorporated by reference into exemplary lens 900. Lens 900 includes transition zone 950, which is considered part of the non-optic peripheral portion 920. Lens 900 does not, in this example, include a central aperture. FIG. 9 illustrates coupling or bonding location 990, generally referring to the annular region where the optic portion 910 is coupled to or bonded to the peripheral portion 920 (exemplary methods of manufacture are described herein). Lens 900 may optionally include any other suitably combinable feature of any of the lenses herein, including any of the dimensions and may also be adapted for any of the vision corrections herein.

Figure 10D:
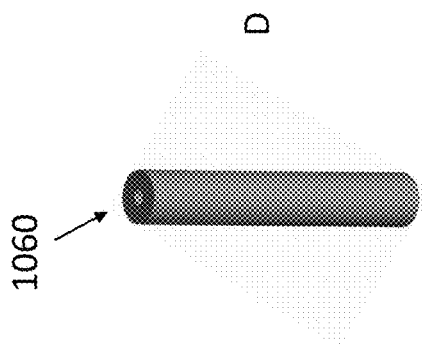
FIGS. 10A-10F illustrate an exemplary method of manufacturing a lens.
Figure 10C:
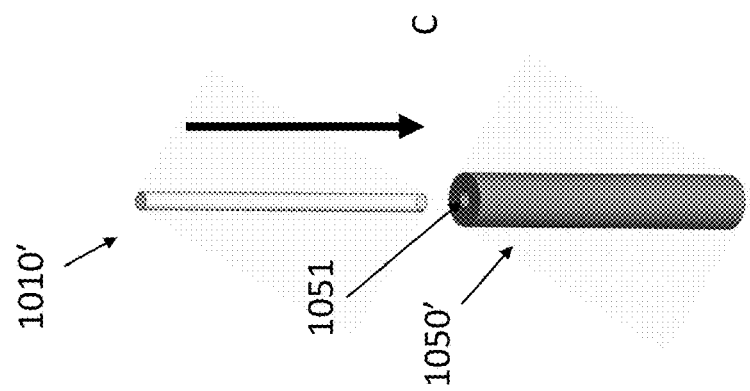
Figure 10A:
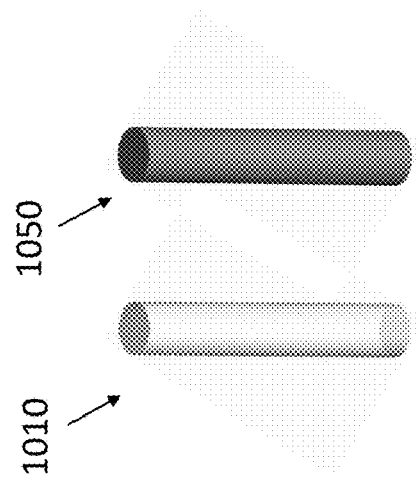
Figure 10B:
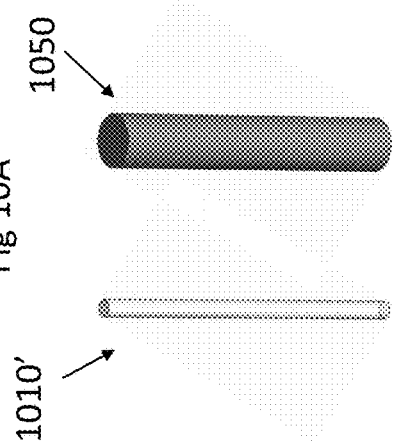
Figure 10F:
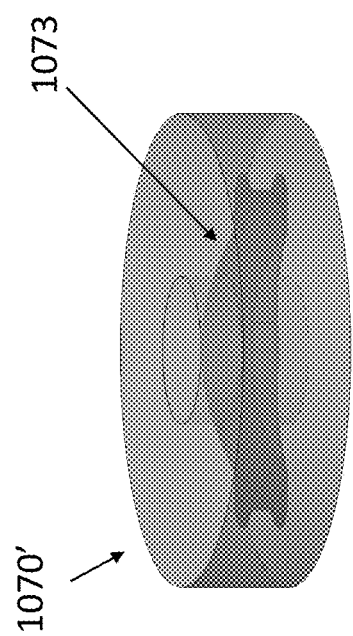
Figure 10E:
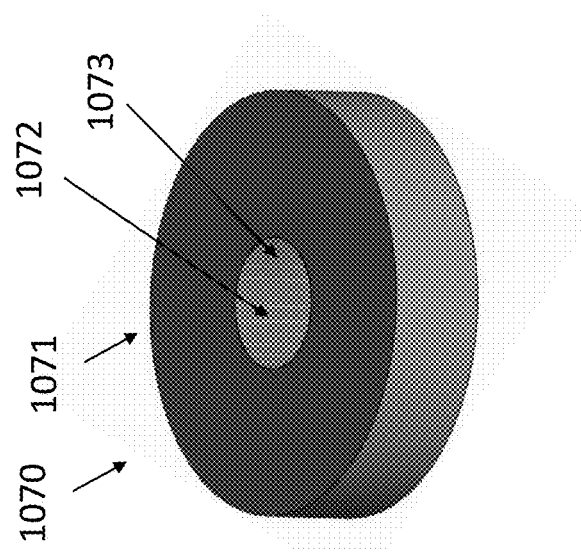

The disclosure herein also includes methods of manufacturing any of the lenses herein. FIGS. 10A-10F illustrate an exemplary sequence of manufacturing that may optionally be used to manufacture any of the lenses herein that include an opaque peripheral portion that includes one or more visible light absorbing materials. The methods may include coupling an optic portion material to a peripheral non-optic portion material. In some embodiments the optic portion material is chemically coupled or connected to the peripheral non-optic portion material. An exemplary method of manufacturing may include creating rods of the starting materials for the optic and non-optic portions. The rods may be made of materials that have the same or substantially the same swell index (details of which are described herein), and wherein one of the rods includes a visible light absorbing component or agent. For example, FIG. 10A illustrates a peripheral portion rod 1050 that is made of a visible light absorbing material, and a starting optic rod 1010 that is made of transparent material. FIG. 10B illustrates optic rod 1010' that has been formed by reducing the diameter of the starting rod 1010 to be the desired diameter of the optic of the lens. Both of rods 1010 and 1010' may be considered optic rods as that phrase is used herein, even though rod 1010' in this example is the rod that is sized with the desired diameter of the lens optic. FIG. 10C illustrates peripheral portion rod 1050' after a cylindrical hole or channel 1051 has been created longitudinally through rod 1050. FIG. 10C also illustrates rod 1010' about to being positioned into the channel 1051, in the direction of the arrow shown. The material of the optic rod 1010' may then be adhered or bonded to the material of the peripheral rod 1050', as shown in FIG. 10D, which may also be considered as a "composite" rod. FIG. 10D may also represent the optic rod after it has been inserted into the peripheral rod but before bonding. Once the optic material is bonded to the peripheral material, they are considered to be coupled together. FIG. 10E illustrates a button 1070 that has been created by cutting a small section from the composite rod shown in FIG. 10D. Button 1070 includes a central transparent section 1072 and a peripheral section 1071 that is coupled to the central section 1072 at coupling location 1073, which is an annular region. The ophthalmic lens 1073 may then be formed from the button 1070 using a variety of surface forming steps, such as lathing and/or milling the desired optical and non-optical surfaces of the optic and the peripheral portion. The exemplary method shown in FIGS. 10A-10F may be used to manufacture any of the lenses described herein. Additionally, if an optic rod is first created to have a desired diameter, it may not be necessary to reduce the diameter as shown in the transition from FIG. 10A to FIG. 10B. It is thus understood that this step may not necessarily be needed in this exemplary method. Additionally, the peripheral portion and the optic portion (of any of the lenses herein) should preferably (but not necessarily) have a common, or the same, axis so that when they are coupled together their axes are aligned.

It is also understood that methods of manufacturing that are described and claimed herein need not necessarily include all of the steps from FIGS. 10A-10E. For example, methods of manufacturing herein may include positioning an optic rod into a cylindrical channel (e.g., as shown by the arrow in FIG. 10C), and bonding or adhering the optic rod to the peripheral portion rod to form an adhered or composite rod with a central transparent region and a peripheral visible light absorbing region, an example of which is shown in FIG. 10D.

As an alternative to the peripheral portions herein that are made of one or more light absorbing materials, the peripheral portions may optionally have one or more surfaces adapted to scatter light, and adapted such that the scattered light is not incorrectly focused. For example, the scattering surfaces may be adapted to cause incident light to scatter in a generally random manner such that no particular direction is preferred. Peripheral portions with one or more scattering surfaces may optionally be made of the same material as the optic, and the lenses may be manufactured as a one-piece lens. After the lens is manufactured, one of more of the peripheral portion surfaces may then be modified such that it is adapted to scatter light. An exemplary non-limiting manner to create the scattering surfaces is to, generally speaking, roughen the surfaces. One or both of an anterior surface and a posterior surface of the peripheral portion may be adapted for scattering as set forth herein.

The invention claimed is:

1. A phakic posterior chamber ophthalmic implant sized and configured for implantation in posterior chamber of a patient's eye, comprising:
   a transparent optic portion that is designed to provide a refractive correction, the transparent optic portion including a central hole that is sized and positioned to provide for flow of aqueous humor through the lens, wherein the transparent optic portion is hydrophilic, has a diameter from 1 mm to 7 mm, and has a central thickness from 100 microns to 400 microns; and an opaque peripheral non-optic portion coupled to the optic portion and extending peripherally therefrom, the peripheral non-optic portion sized and configured to engage a sulcus of an eye, the transparent optic portion made of a transparent optic material adapted to allow visible light to pass therethrough, and an entirety of the peripheral non-optic portion made of a light absorbing material adapted to absorb visible light, wherein the transparent optic material and the visible light absorbing material have linear swell indices that are within 5% of each other when exposed to one or both of aqueous humor or balanced salt solution ('BSS'), wherein the transparent optic material and the peripheral portion material comprise the same constituent components except that the peripheral non-optic portion material includes one or more light absorbing components, wherein the peripheral portion comprises a plate haptic extending all the way from a periphery of the optic portion to a radially outermost surface of the phakic posterior chamber ophthalmic lens, wherein the radially outermost surface of the plate haptic comprises a sulcus-engaging surface.

2. The phakic posterior chamber ophthalmic implant of claim 1, wherein the transparent material and the visible light absorbing material have linear swell indices that are within 1% of each other when exposed to one or both of aqueous humor or balanced salt solution ('BSS').

3. The phakic posterior chamber ophthalmic implant of claim 1, wherein the transparent optic material is bonded to the light absorbing material.

4. The phakic posterior chamber ophthalmic implant of claim 1, wherein the peripheral portion includes a transition zone adjacent to the optic portion.

5. The phakic posterior chamber ophthalmic implant of claim 1, wherein the transparent optic portion has a diameter based on the visual impairment the phakic posterior chamber ophthalmic implant is designed to treat.

6. The phakic posterior chamber ophthalmic implant of claim 1, wherein the lens has a width from 10 mm to 14 mm.

7. The phakic posterior chamber ophthalmic implant of claim 1, wherein the lens is shaped to correct ametropia.

8. The phakic posterior chamber ophthalmic implant of claim 7, wherein the transparent optic portion is configured as an extended depth of field optic to treat presbyopia.

9. The phakic posterior chamber ophthalmic implant of claim 1, wherein the lens is shaped to correct myopia.

10. The phakic posterior chamber ophthalmic implant of claim 9, wherein the lens is shaped to also correct astigmatism.

11. The phakic posterior chamber ophthalmic implant of claim 10, wherein the transparent optic portion is configured as an extended depth of field optic to treat presbyopia.

12. The phakic posterior chamber ophthalmic implant of claim 9, wherein the transparent optic portion is configured as an extended depth of field optic to treat presbyopia.

13. The phakic posterior chamber ophthalmic implant of claim 1, wherein the lens is shaped to correct hyperopia.

14. The phakic posterior chamber ophthalmic implant of claim 13, wherein the transparent optic portion is configured as an extended depth of field optic to treat presbyopia.

15. The phakic posterior chamber ophthalmic implant of claim 13, wherein the lens is shaped to also correct astigmatism.

16. The phakic posterior chamber ophthalmic implant of claim 15, wherein the transparent optic portion is configured as an extended depth of field optic to treat presbyopia.

17. The phakic posterior chamber ophthalmic implant of claim 1, wherein the lens is shaped to correct astigmatism.

18. The phakic posterior chamber ophthalmic implant of claim 17, wherein the transparent optic portion is configured as an extended depth of field optic to treat presbyopia.

19. The phakic posterior chamber ophthalmic implant of claim 1, wherein a thickness of a peripheral region of the peripheral non-optic portion where it engages the sulcus is between 50 microns and 200 microns.

* * * * *